(12) United States Patent
Keren et al.

(10) Patent No.: US 8,449,559 B2
(45) Date of Patent: May 28, 2013

(54) METHOD FOR SUTURING

(75) Inventors: Dvir Keren, Tel Aviv (IL); Rami Lore, Tiv'on (IL)

(73) Assignee: Neatstitch Ltd., Orakiva (IL)

( * ) Notice: Subject to any disclaimer, the term of this patent is extended or adjusted under 35 U.S.C. 154(b) by 0 days.

(21) Appl. No.: 13/204,684

(22) Filed: Aug. 7, 2011

(65) Prior Publication Data
US 2012/0016385 A1 Jan. 19, 2012

Related U.S. Application Data

(62) Division of application No. 11/569,155, filed as application No. PCT/IL2005/000070 on Jan. 20, 2005, now Pat. No. 8,034,060.

(60) Provisional application No. 60/573,631, filed on May 21, 2004.

(51) Int. Cl.
*A61B 17/04* (2006.01)
*A61B 17/08* (2006.01)
*A61B 17/00* (2006.01)

(52) U.S. Cl.
CPC ......... *A61B 17/0469* (2013.01); *A61B 17/0482* (2013.01); *A61B 17/0057* (2013.01)
USPC .......................................... 606/144; 606/213

(58) Field of Classification Search
USPC .......... 606/232, 153, 213, 151, 142, 144–150
See application file for complete search history.

(56) References Cited

U.S. PATENT DOCUMENTS

| | | | |
|---|---|---|---|
| 4,621,640 A | 11/1986 | Mulhollan et al. |
| 5,320,632 A | 6/1994 | Heidmueller |
| 5,364,408 A | 11/1994 | Gordon |
| 5,368,601 A | 11/1994 | Sauer et al. |
| 5,411,481 A | 5/1995 | Allen et al. |

(Continued)

FOREIGN PATENT DOCUMENTS

| | | |
|---|---|---|
| EP | 0738127 | 1/2004 |
| JP | 8033635 A | 2/1996 |

(Continued)

OTHER PUBLICATIONS

Japanese Patent Application # 2007517643 Official Action dated Oct. 13, 2010.

(Continued)

*Primary Examiner* — Tuan V Nguyen
(74) *Attorney, Agent, or Firm* — D. Kligler I.P. Services Ltd.

(57) ABSTRACT

A suture insertion device (120) includes a shaft (124), which is adapted to be inserted into a body cavity (154). First and second needles (160) hold respective first and second ends of a suture thread (122). First and second needle guides (130) are attached to the shaft and respectively hold the first and second needles. The needle guides have a first operative configuration in which the needle guides are held parallel to the axis of the shaft for insertion of the shaft into the body cavity and a second operative configuration in which the needle guides are deployed outward from the shaft within the body cavity so as to point the needles in a proximal direction. An ejector (164) is operative to eject the needles from the needle guides in the second operative configuration so as to cause the needles to penetrate tissue (156) adjoining the body cavity.

32 Claims, 28 Drawing Sheets

U.S. PATENT DOCUMENTS

| | | | |
|---|---|---|---|
| 5,417,600 | A | 5/1995 | Maegawa et al. |
| 5,417,699 | A | 5/1995 | Klein et al. |
| 5,458,609 | A | 10/1995 | Gordon et al. |
| 5,470,338 | A | 11/1995 | Whitfield et al. |
| 5,575,800 | A | 11/1996 | Gordon |
| 5,578,044 | A | 11/1996 | Gordon et al. |
| 5,700,272 | A | 12/1997 | Gordon et al. |
| 5,713,910 | A | 2/1998 | Gordon et al. |
| 5,741,277 | A | 4/1998 | Gordon et al. |
| 5,836,955 | A | 11/1998 | Buelna et al. |
| 5,868,762 | A | 2/1999 | Cragg et al. |
| 5,924,424 | A | 7/1999 | Stevens et al. |
| 6,048,351 | A | 4/2000 | Gordon et al. |
| 6,245,079 | B1 | 6/2001 | Nobles et al. |
| 6,346,111 | B1 | 2/2002 | Gordon et al. |
| 6,401,720 | B1 | 6/2002 | Stevens et al. |
| 6,451,031 | B1 | 9/2002 | Kontos |
| 6,517,553 | B2 | 2/2003 | Klein et al. |
| 6,743,241 | B2 | 6/2004 | Kerr |
| 6,939,357 | B2 | 9/2005 | Navarro et al. |
| 6,997,932 | B2 | 2/2006 | Dreyfuss et al. |
| 7,033,370 | B2 | 4/2006 | Gordon et al. |
| 7,048,747 | B2 | 5/2006 | Arcia et al. |
| 7,060,077 | B2 | 6/2006 | Gordon et al. |
| 2006/0052801 | A1 | 3/2006 | Dreyfuss et al. |

FOREIGN PATENT DOCUMENTS

| | | |
|---|---|---|
| JP | 2002336264 A | 11/2002 |
| JP | 2003093394 A | 4/2003 |
| JP | 2003310537 A | 11/2003 |
| JP | 2005074169 A | 3/2005 |
| WO | 9405213 A1 | 3/1994 |
| WO | 0056223 | 9/2000 |
| WO | 2005055801 | 9/2000 |

OTHER PUBLICATIONS

International Application PCT/IL2005/000070 Search Report dated Feb. 20, 2007.

Australian Patent Application # 2005244677 Official Action dated Feb. 22, 2010.

U.S. Appl. No. 11/569,155 Official Action dated Jan. 7, 2011.

Japanese Patent Application # 2007517643 Official Action dated Apr. 13, 2011.

Canadian Patent Application # 2562862 Official Action dated Sep. 29, 2011.

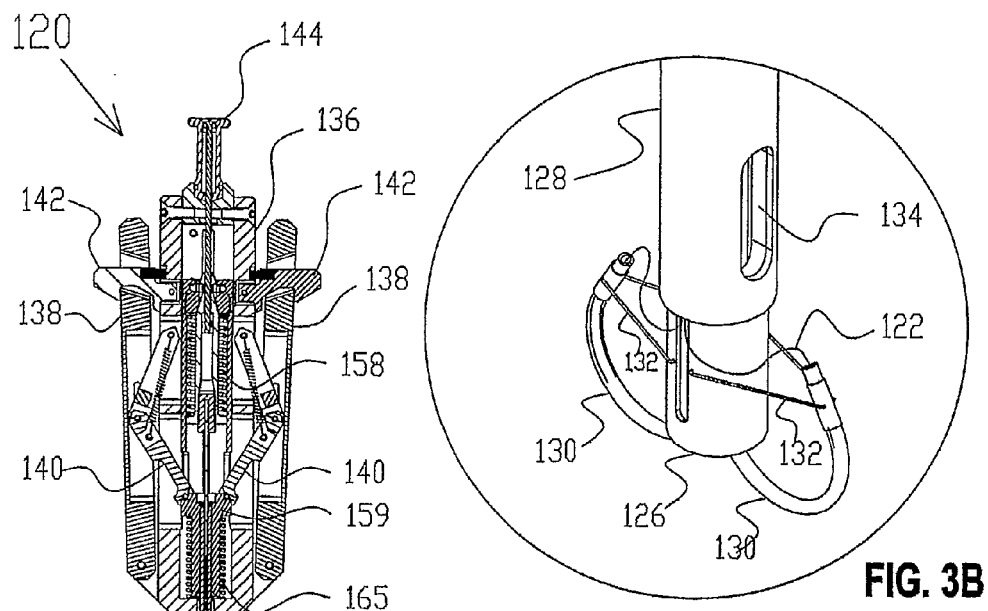
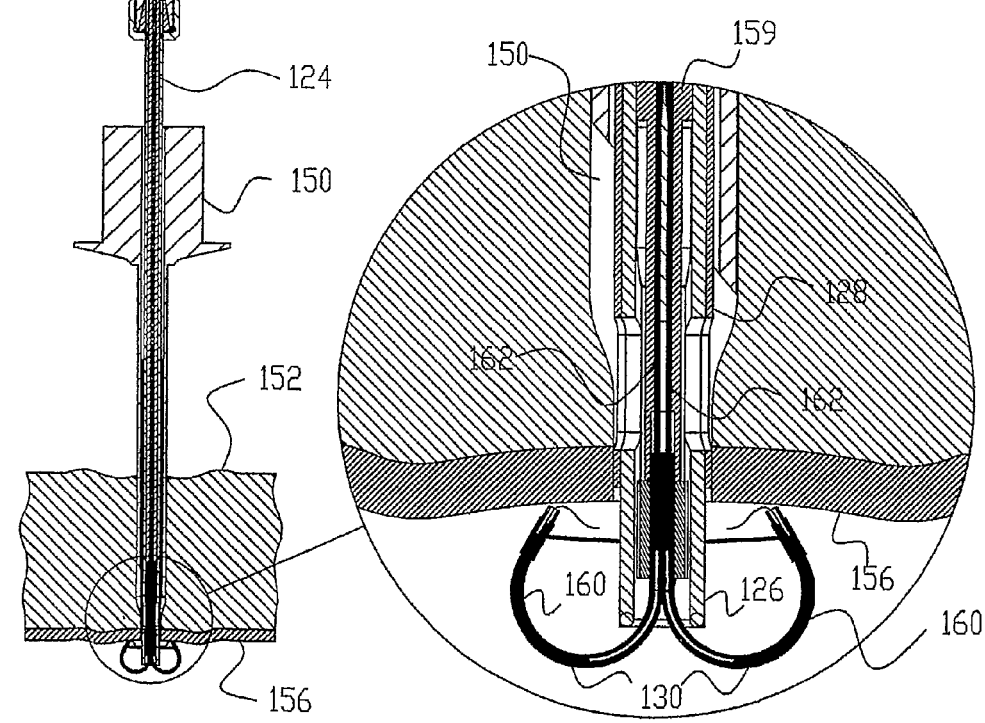
FIG. 3A

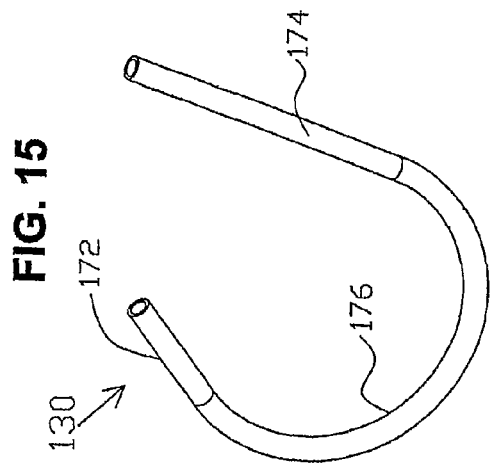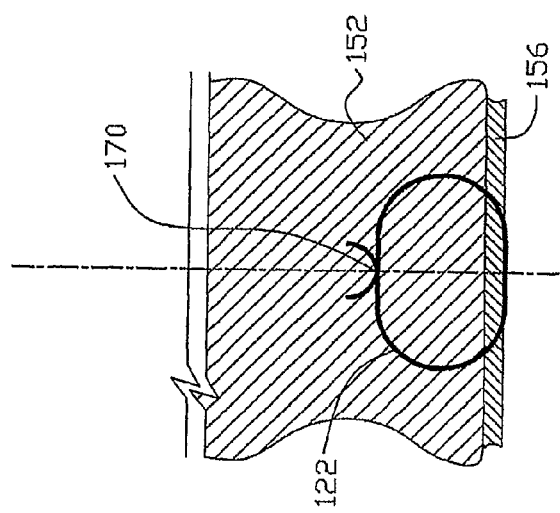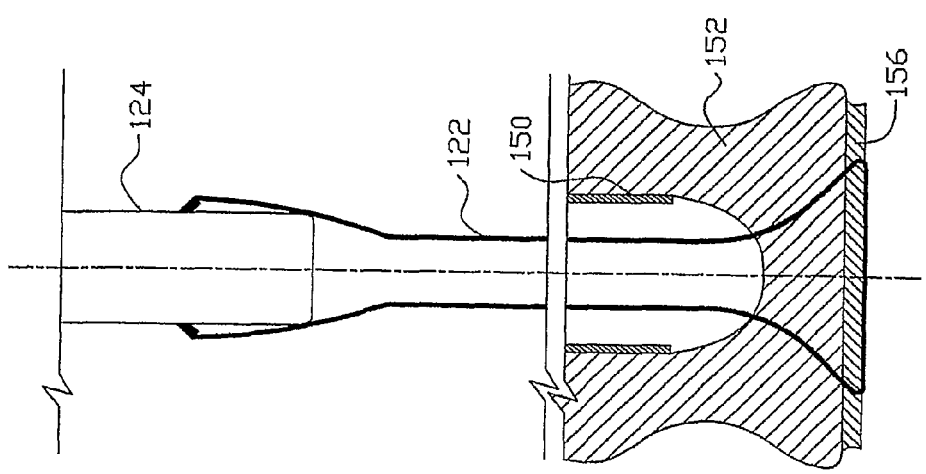

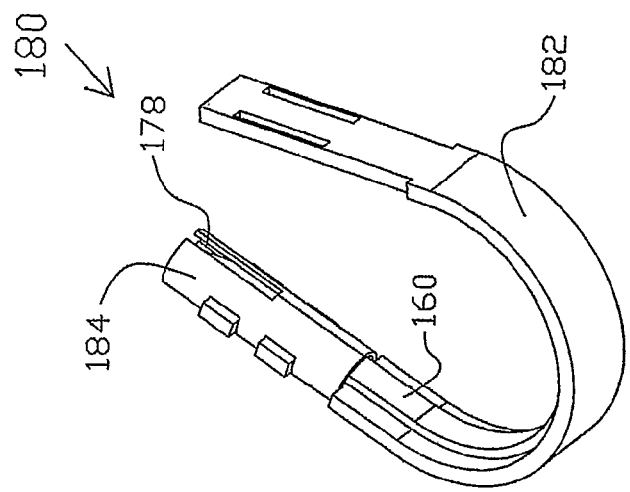
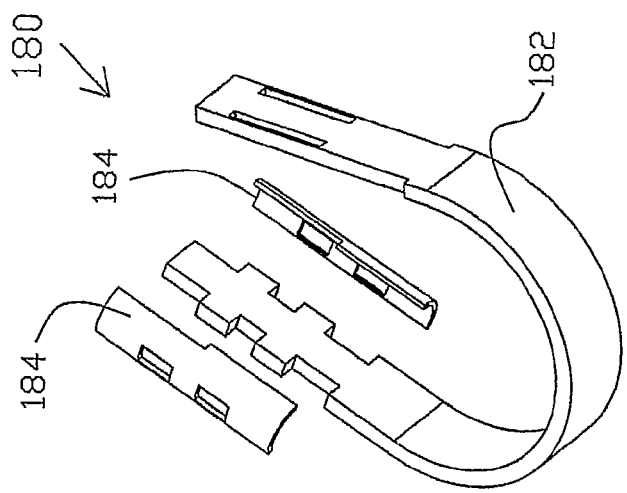
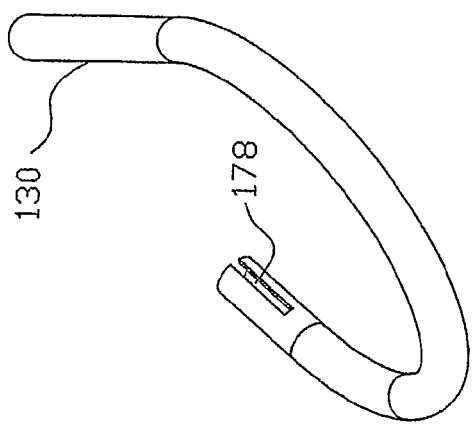

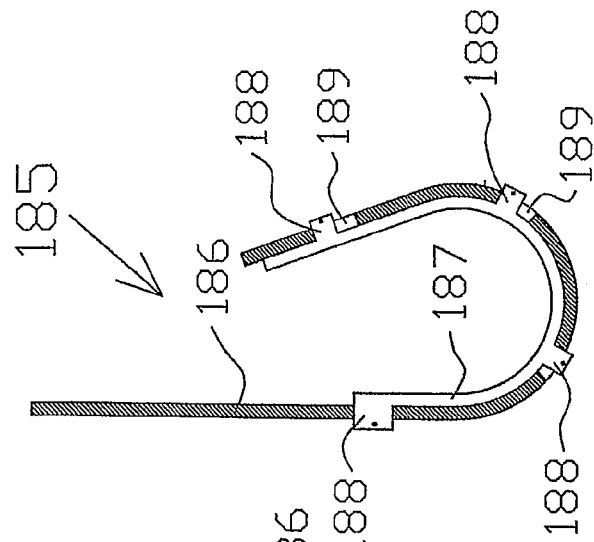
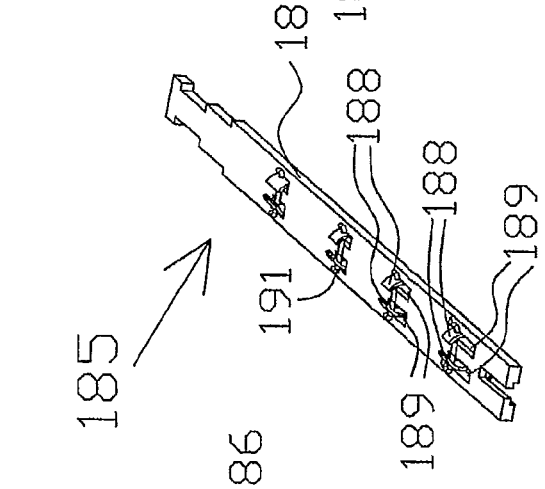
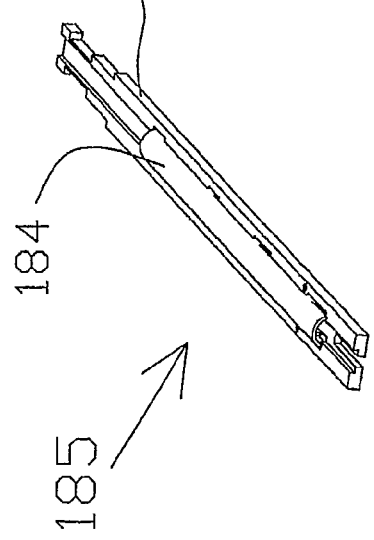
FIG. 18A
FIG. 18B
FIG. 18C

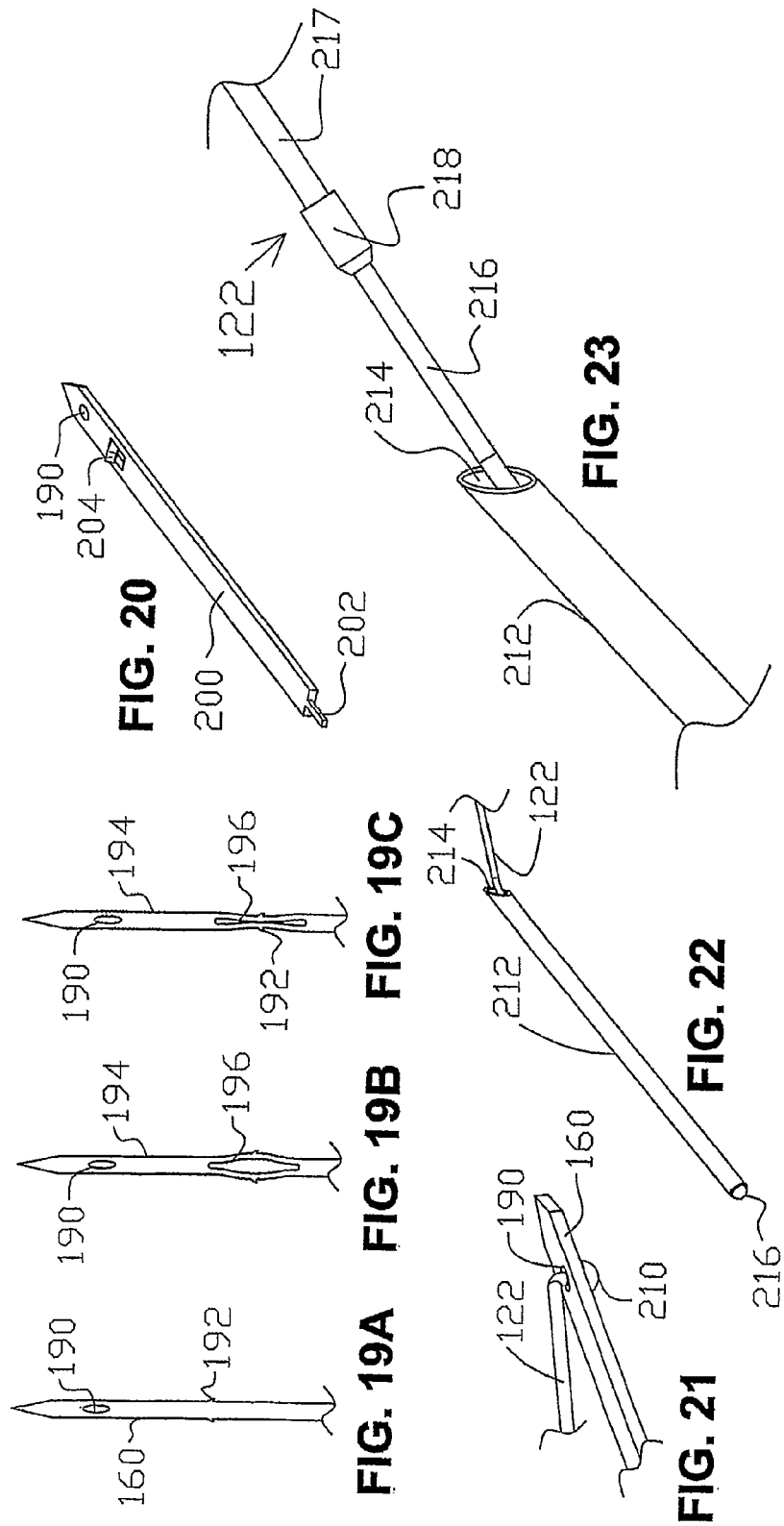

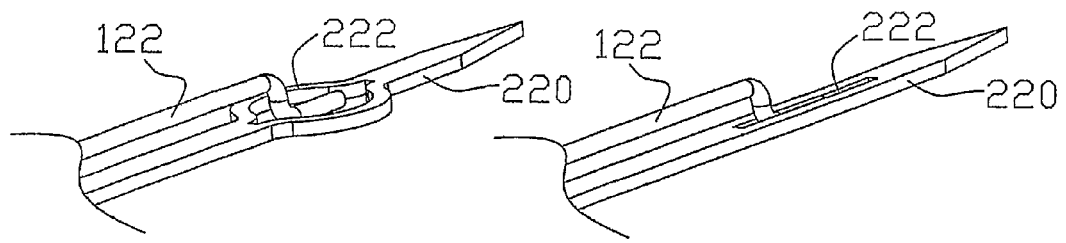
FIG. 24A  FIG. 24B
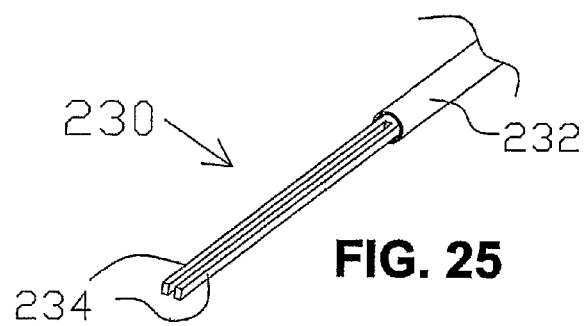
FIG. 25
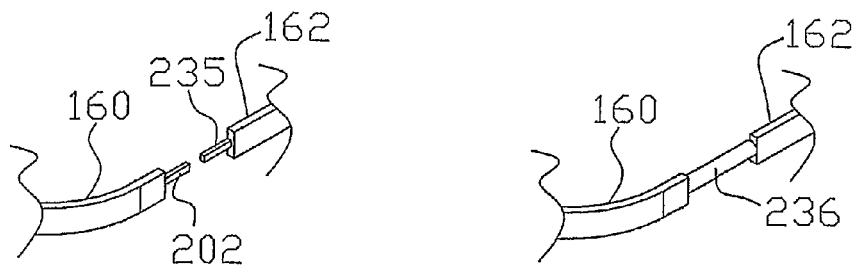
FIG. 26A  FIG. 26B

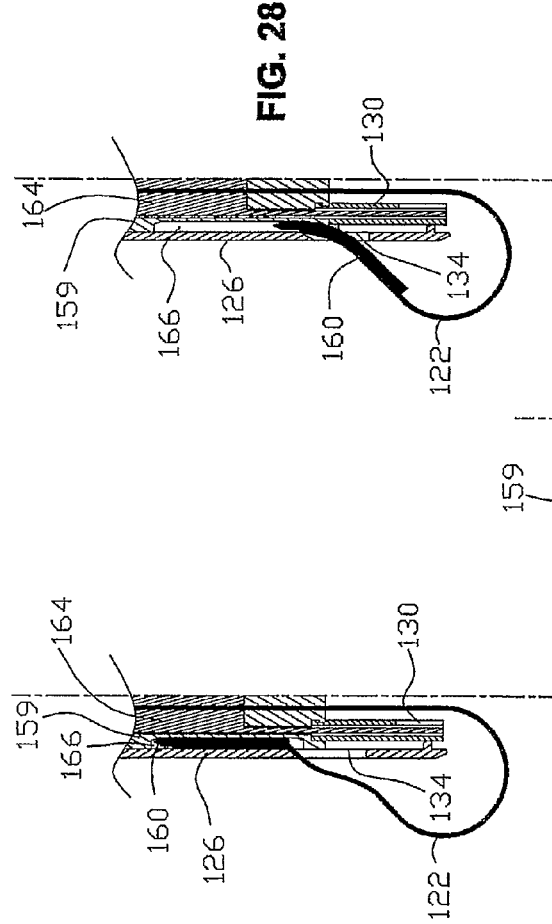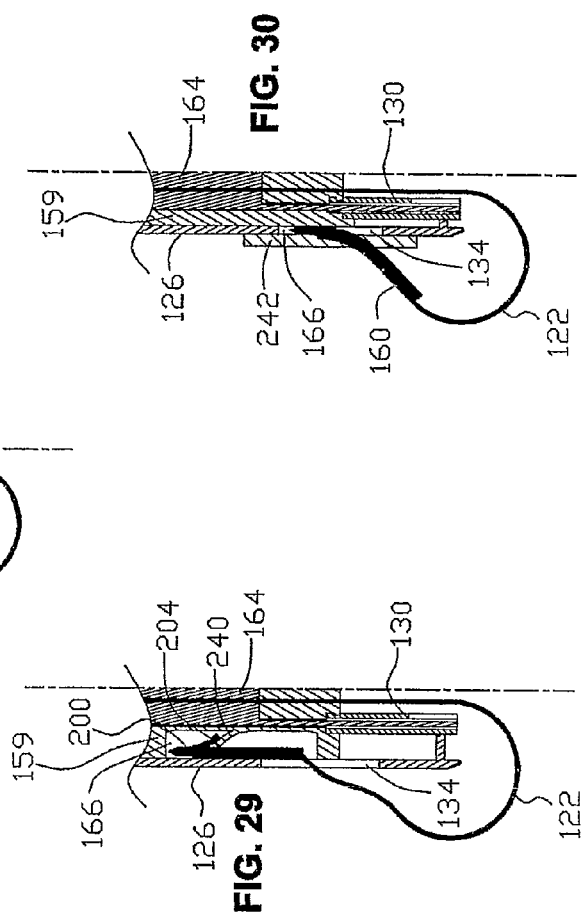

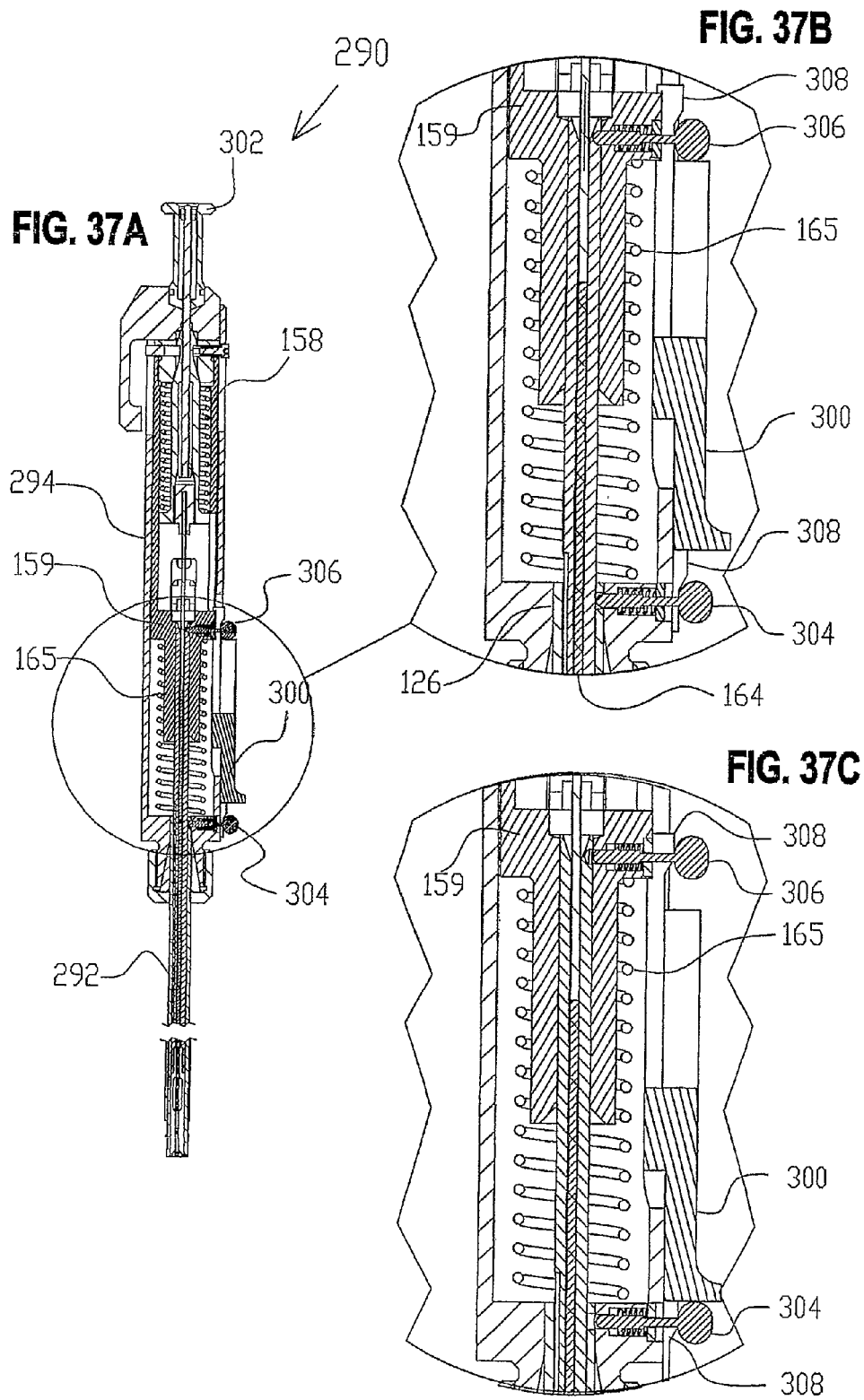

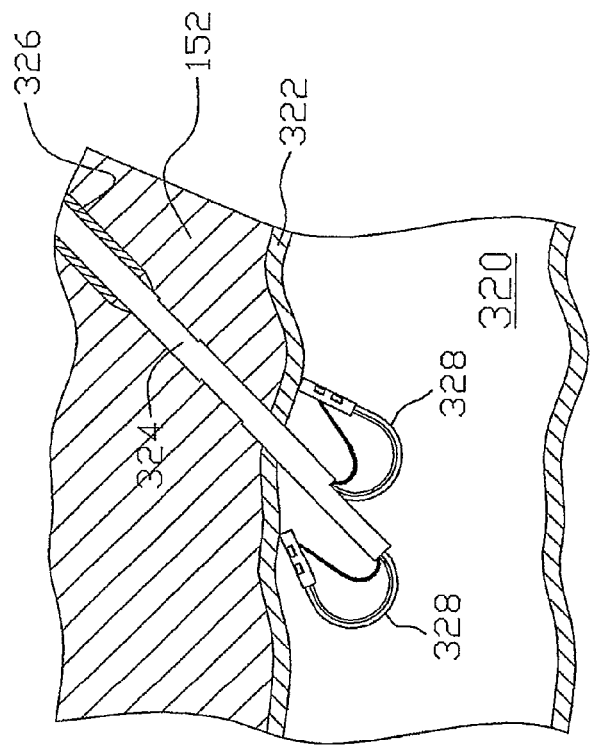
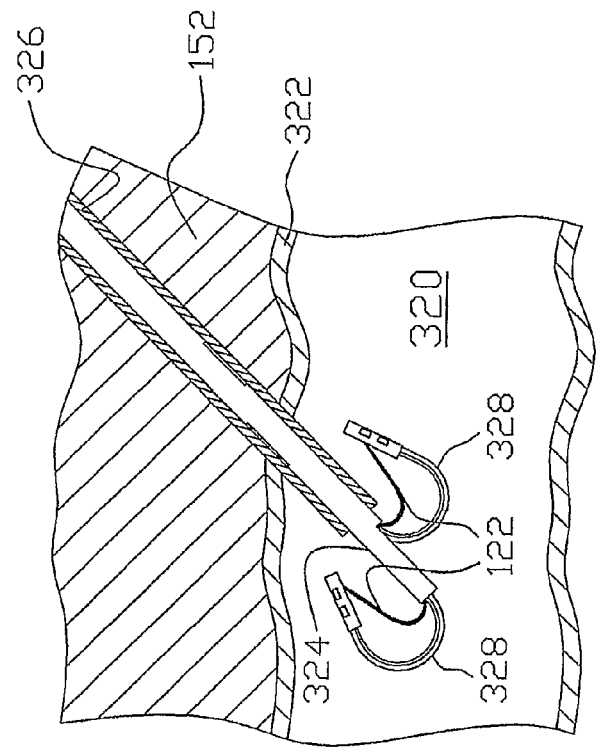

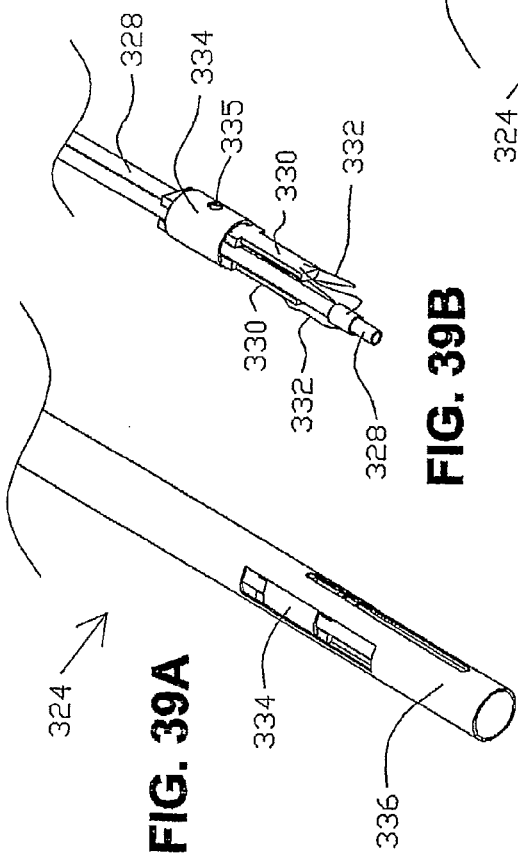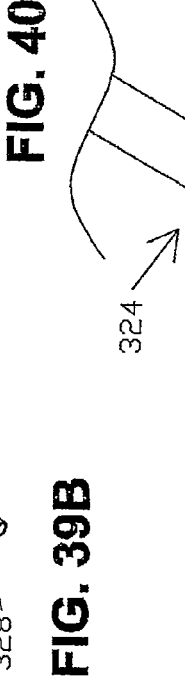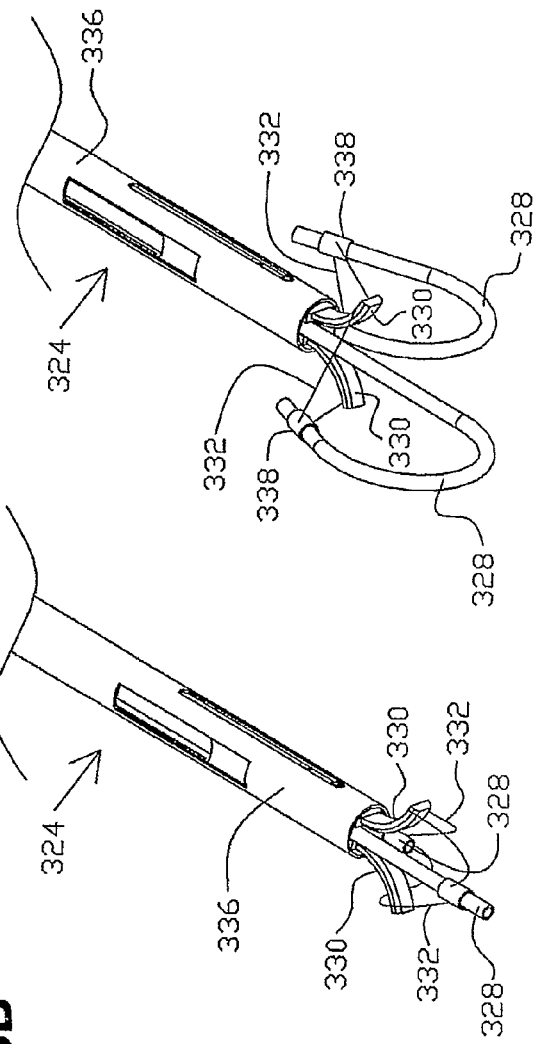

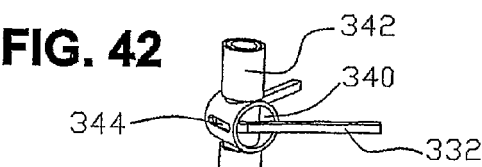
FIG. 42
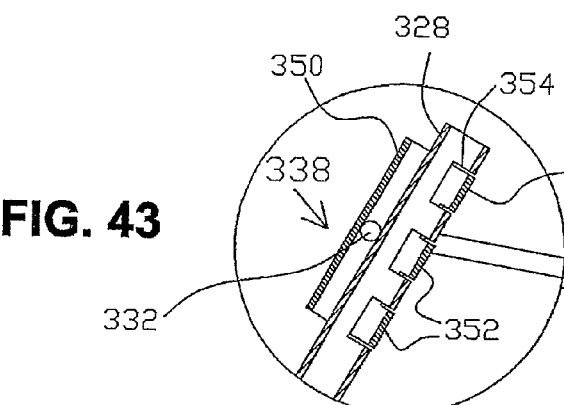
FIG. 43
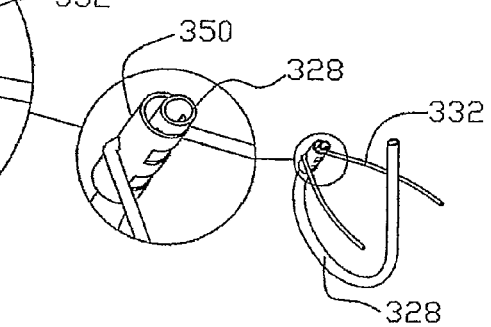
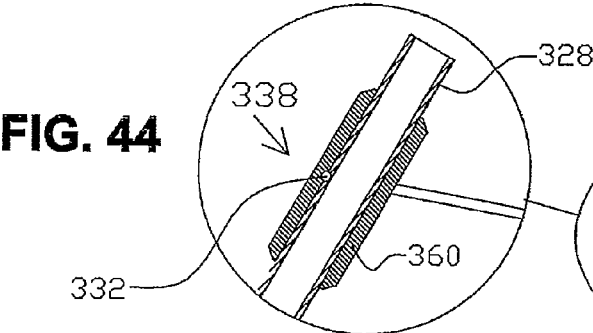
FIG. 44
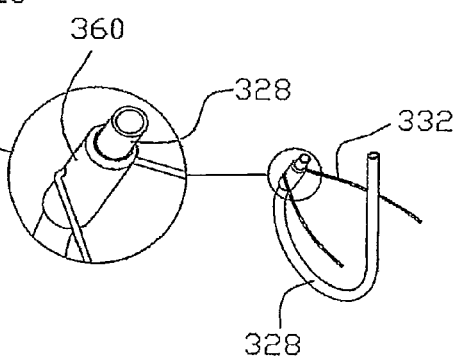
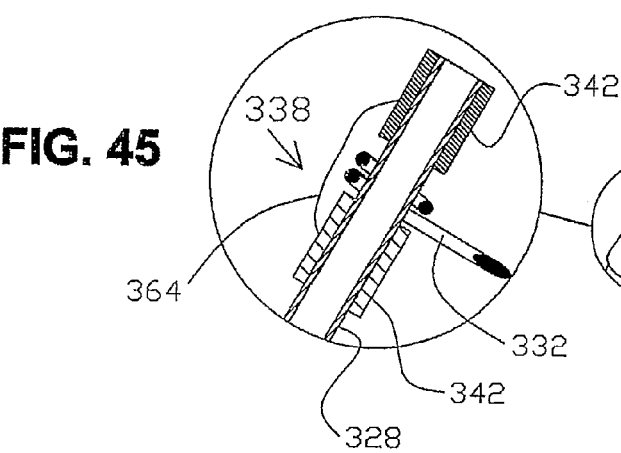
FIG. 45
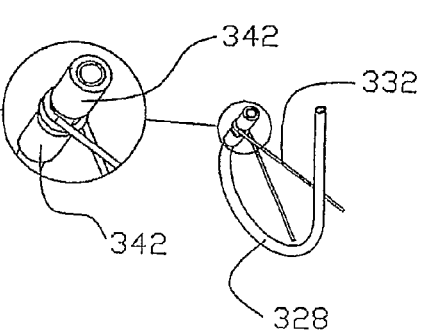

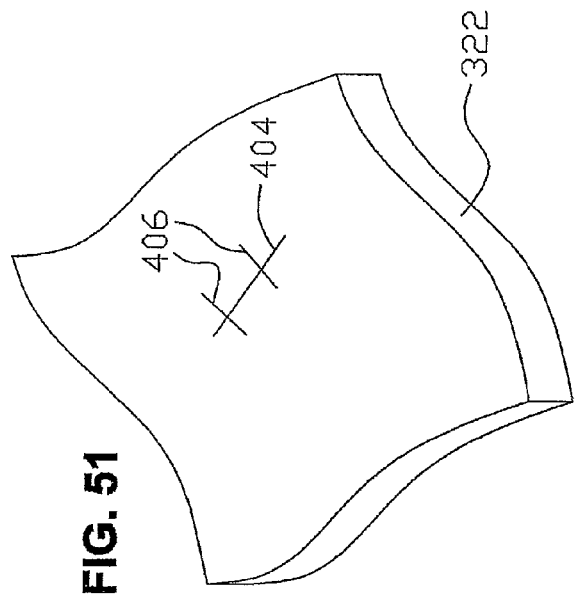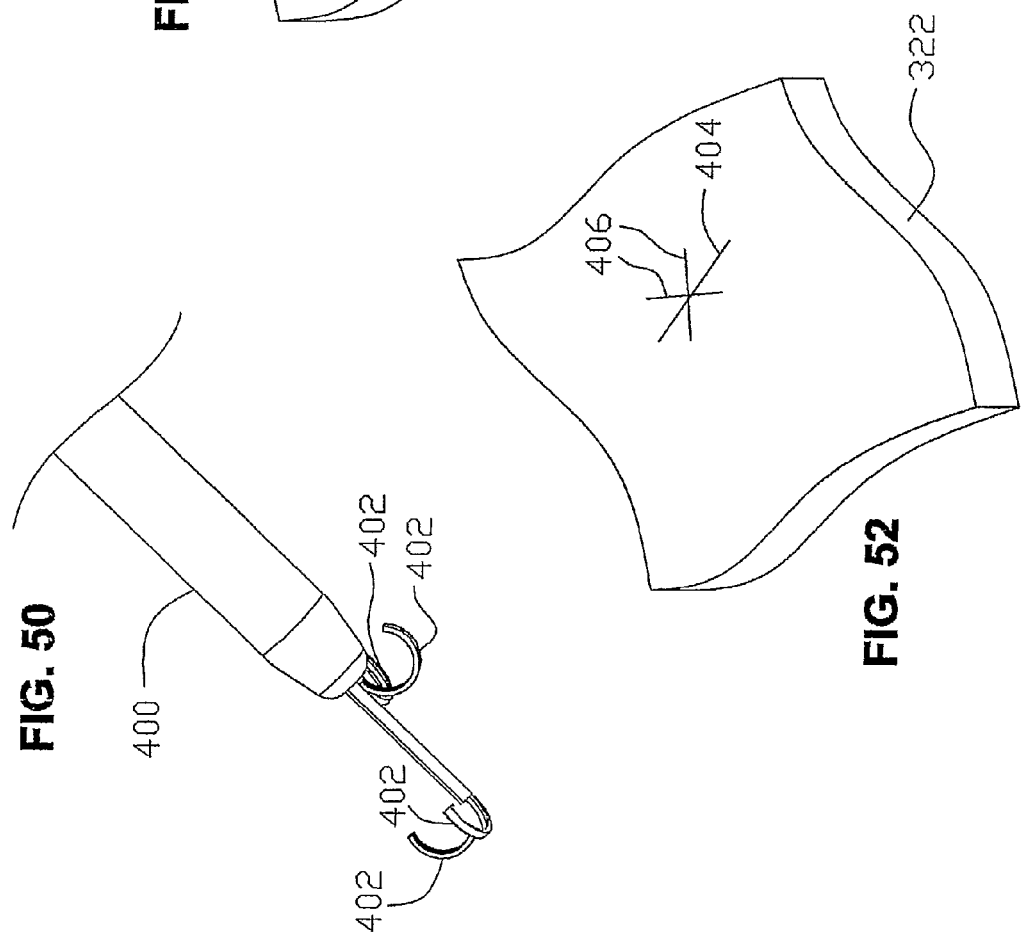

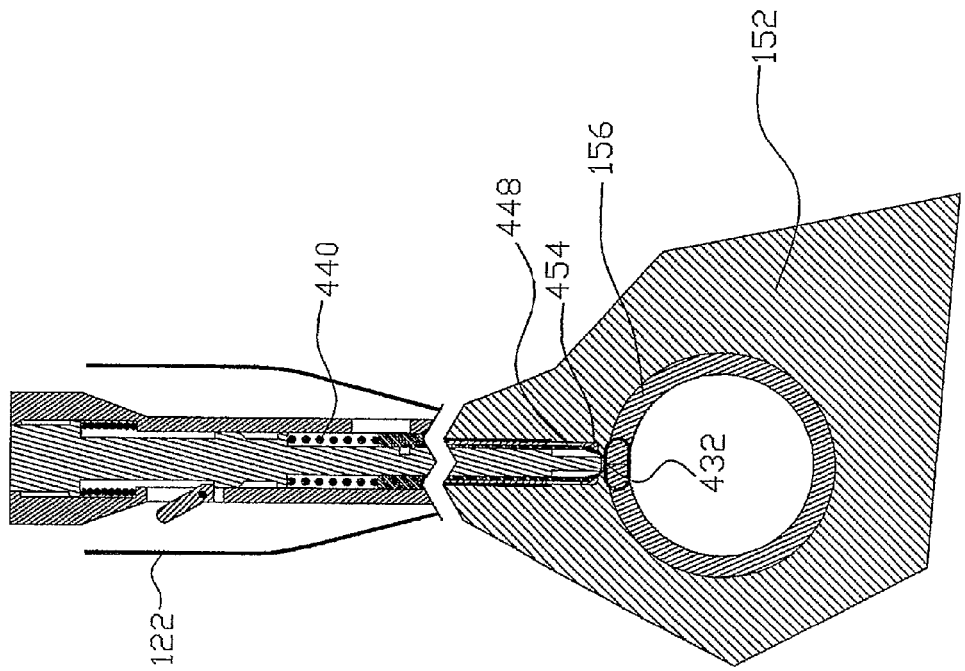
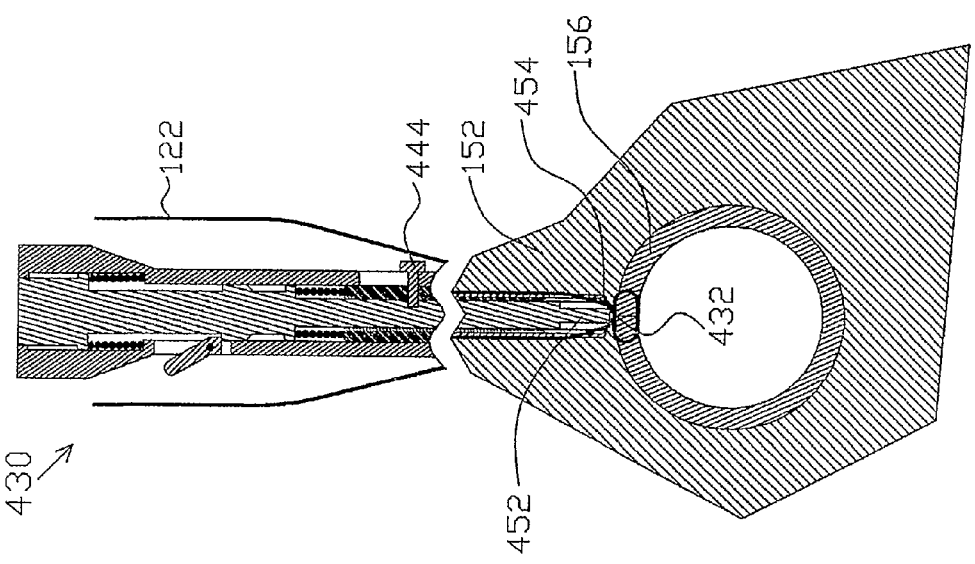

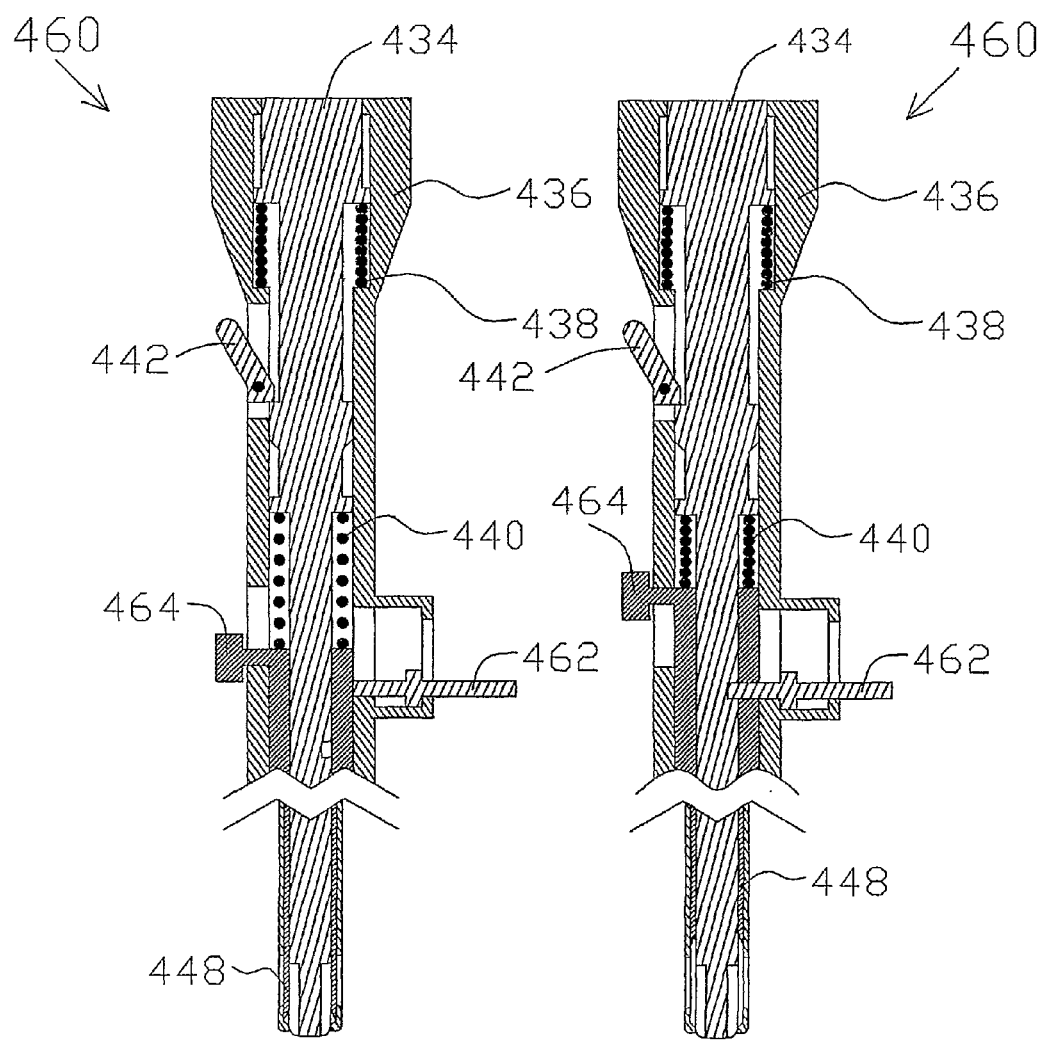

METHOD FOR SUTURING

CROSS-REFERENCE TO RELATED APPLICATIONS

This application is a division of U.S. patent application Ser. No. 11/569,155, filed in the national phase of PCT Patent Application PCT/IL2005/000070, which claims the benefit of U.S. Provisional Patent Application 60/573,631, filed May 21, 2004, which is incorporated herein by reference.

FIELD OF THE INVENTION

The present invention relates generally to medical devices, and specifically to minimally-invasive suturing devices and techniques.

BACKGROUND OF THE INVENTION

Minimally-invasive surgical procedures frequently involve insertion of instruments into a body cavity through a tissue puncture site. Examples of such procedures include insertion of vascular catheters through a puncture site in a blood vessel and insertion of laparoscopic instruments through a puncture site in the abdominal wall. (In the context of the present patent application and in the claims, the term "cavity" is used broadly to refer to any and all sorts of volumes inside the body, including lumens, such as blood vessels.) It is desirable, in order to facilitate healing and reduce complications, to suture the puncture site shut at the end of the procedure. Although the skin at the outer end of the puncture can easily be sutured, it is difficult to access and suture the internal tissues (such as the intima of the blood vessel or the abdominal fascia) through the puncture. Therefore, at the end of a vascular catheterization procedure, for example, many cardiologists and invasive radiologists simply press on the puncture site mechanically to achieve homeostasis. This mechanical technique requires the patient to remain immobilized for a long time (typically 2-8 hours), and increases the risk of subsequent bleeding.

A number of specialized instruments have been developed for percutaneous suturing of vascular puncture sites. For example, U.S. Pat. No. 5,417,600, whose disclosure is incorporated herein by reference, describes a suture applying device that comprises a shaft with a pair of needles near its distal end. The needles are joined by a length of suture. The shaft is used to introduce the needles into a lumen of a body structure and then to push the needles back through tissue on either side of the puncture site. After the needles have passed through the tissue, they are drawn outward, leaving a loop of suture behind to close the puncture site.

As another example, U.S. Pat. No. 5,868,762, whose disclosure is incorporated herein by reference, describes a device for suturing a vascular puncture site. The device includes a shaft having a distal end terminating in a pair of resilient prongs. Each of the prongs carries a suture anchor, attached to one end of a suture. The shaft is introduced into the puncture site, whereupon the prongs expand to an open position, thus positioning the suture anchors for penetration of the vascular wall by manipulation of the shaft. The prongs are then retracted, leaving the suture anchors to secure the sutures to the vascular wall tissue.

U.S. Pat. No. 6,245,079, whose disclosure is incorporated herein by reference, describes a suturing device having a distal portion that is inserted percutaneously through an incision into a blood vessel. The distal portion has two retractable arms, which extend and hold a suture within the blood vessel. Retractable needles are deployed from the device to pierce the vessel wall, release the suture ends from the retractable arms, and then pull the suture through the vessel wall.

Other exemplary devices and methods for suturing internal puncture sites are described in U.S. Pat. Nos. 6,517,553, 6,451,031 and 5,411,481, whose disclosures are incorporated herein by reference.

SUMMARY OF THE INVENTION

Embodiments of the present invention that are disclosed hereinbelow provide devices and methods for suturing a puncture site in the body of a patient with enhanced safety and convenience.

In these embodiments, a suture insertion device comprises a shaft, which is inserted by an operator through the puncture so that the distal end of the shaft protrudes into an underlying body cavity. The shaft carries, at its distal end, a pair of flexible needles, which are held by respective needle guides. Each needle holds one end of a suture. Typically, during insertion of the shaft through the puncture, the needle guides are held straight and parallel to the axis of the shaft, so that the device maintains a narrow profile. In some embodiments, the needle guides comprise a resilient material, such as a superelastic material. The resilient needle guides are produced in a curved form, but are forced to remain generally straight and parallel within the shaft during insertion of the shaft through the puncture.

Once the distal end of the shaft is inside the cavity, the needle guides are deployed outward from the shaft. In this configuration, the needle guides point the needles in the proximal direction, i.e., back toward the cavity wall that is to be sutured. In some embodiments, superelastic needle guides are deployed in the distal direction, out of the distal end of the shaft, and are configured to assume a "U" shape upon release from the shaft so as to point the needles in the desired proximal direction. The ends of the needle guides are then brought into contact with the cavity wall. Typically, the needles are contained within the needle guides, so that the points of the needles do not contact the cavity wall or other tissues within the cavity during the stage of the procedure.

When the needle guides are properly positioned, the operator actuates an ejector in the shaft to eject the needles rapidly from the needle guides in the proximal direction. Typically, the needles comprise an elastic material, which straightens as the needles exit the needle guides. The needles penetrate the cavity wall, thus drawing the suture through the wall at respective points on either side of the puncture. In some embodiments, the needles are aimed to engage the sides of the shaft after penetrating the cavity wall and are then captured alongside or in the shaft. The needle guides (now empty) are pulled back into the shaft, and the device is withdrawn from the body, pulling the suture ends with it. The suture is then tied to close the internal puncture.

The use of needles and needle guides in the manner described herein gives embodiments of the present invention substantial advantages over suturing devices known in the art. For example, ejection of the needles in the proximal direction eliminates the risk of accidentally puncturing other surfaces or organs deeper inside the body. Furthermore, because the needles remain inside the needle guides until the needle guides actually contact the cavity wall that is to be sutured, the risk that the needles will accidentally catch and suture other tissues to the cavity wall is also reduced. The needle guides may be made stiff enough to provide precise control of the locations at which the needles penetrate the cavity wall, while the needles themselves may be very thin and flexible in order to reduce trauma and bleeding when they do penetrate the tissue.

Although the embodiments described herein relate particularly to closure of punctures in body cavities, such as blood vessels or the abdominal cavity, the principles of the present invention may also be applied in closing holes of other types in body tissue, as well as performing other functions in minimally-invasive surgery.

There is therefore provided, in accordance with an embodiment of the present invention, a suture insertion device, including:

a shaft, having a longitudinal axis and a distal end, which is adapted to be inserted into a body cavity;

first and second needles, which are configured to hold respective first and second ends of a suture thread;

first and second needle guides, which are attached to the shaft and respectively hold the first and second needles, the needle guides having a first operative configuration in which the needle guides are held parallel to the axis for insertion of the shaft into the body cavity and a second operative configuration in which the needle guides are deployed outward from the shaft within the body cavity so as to point the needles in a proximal direction; and an ejector, which is operative to eject the needles from the needle guides in the second operative configuration so as to cause the needles to penetrate tissue adjoining the body cavity.

Typically, the needles have respective points, and the needle guides contain the needles so that the points do not contact the tissue while the needles are held by the needle guides. The needle guides have respective outer ends, and are typically deployed outward from the shaft in the second operative configuration so as to permit an operator of the device to bring the outer ends of the needle guides into engagement with the tissue before ejecting the needles.

In disclosed embodiments, in the second operative configuration, the needle guides curve out of the shaft so as to point in the proximal direction. In some embodiments, the needle guides are deployed from the distal end of the shaft and curve back in the proximal direction.

Typically, the needle guides include a superelastic material, which is formed prior to assembly of the device so as to have a curved shape. In some embodiments, the needle guides include superelastic tubes having lumens that contain the needles. In other embodiments, the needle guides include plates of the superelastic material, and the needles are held against the plates until the needles are ejected. In one such embodiment, the needle guides include covers for holding the needles against the plates, and the covers are attached to the plates so as to shift longitudinally along the plates when the needle guides are deployed from the first operative configuration to the second operative configuration.

Typically, the needles include an elastic material, which is formed so that the needles assume a straight shape upon being ejected from the needle guides.

In some embodiments, the device includes one or more stabilizers, which are contained within the shaft while the needle guides are in the first operative configuration, and which are coupled to be deployed together with the needle guides so as to stabilize the needle guides in the second operative configuration. In one embodiment, the needle guides have outer ends from which the needles are ejected, and the stabilizers include cords, which couple the outer ends of the needle guides to the shaft. The stabilizers may include wings, which extend outward from the distal end of the shaft in a direction transverse to a plane defined by the needle guides, and wherein the cords couple the needle guides to the wings. Additionally or alternatively, the stabilizers may include couplers, which are attached to the outer ends of the needle guides so as to fix the cords to the needle guides. In another embodiment, the stabilizers include struts, which open outward from the shaft in order to hold the needle guides.

In a disclosed embodiment, the first and second needle guides are non-symmetrical in the second operative configuration. Typically, the needle guides have respective outer ends, and are formed so that in the second operative configuration, the outer ends of the first and second needle guides may be brought into simultaneous engagement with the tissue while the shaft is angled obliquely relative to the tissue.

In one embodiment, the suture thread held by the first and second needles is a first thread, and the device includes third and fourth needle guides and third and fourth needles, which are respectively held by the third and fourth needle guides and are configured to hold a second suture thread, wherein the ejector is operative to eject the first, second, third and fourth needles, thereby passing the ends of both the first and second suture threads through the tissue. The first, second, third and fourth needles and the first and second suture threads may be configured so as to produce two parallel stitches through the tissue. Alternatively, the first, second, third and fourth needles and the first and second suture threads may be configured so as to produce two crossed stitches through the tissue.

In some embodiments, the needles are formed from a plate of a flat material. Typically, each of the needles includes an eye, and each of the first and second ends of the suture thread is respectively inserted through and fastened within the eye of one of the first and second needles.

In other embodiments, each of the needles includes a tube. Typically, each of the first and second ends of the suture thread is respectively inserted into and fastened within the tube of one of the first and second needles. In one embodiment, the needles have an outer dimension that is less than or equal to a diameter of the suture thread, and the ends of the suture thread are narrowed for insertion into the tube.

In disclosed embodiments, in the second operative configuration, the needle guides are configured to point the needles toward the shaft, so that the needles strike the shaft after passing through the tissue. Typically, the shaft includes a needle trap, for capturing and holding the needles when the needles strike the shaft. In one embodiment, the needle trap includes a cavity in an outer surface of the shaft. The needles may include a protrusion, which engages the needle trap so as to prevent release of the needles from the needle trap. Additionally or alternatively, the needle trap includes an elastomeric material, which is penetrated by the needles when the needles strike the shaft.

In some embodiments, the ejector includes first and second ejector ends and is configured to drive the first and second ejector ends into the first and second needle guides, respectively, in order to eject the needles. In one embodiment, each of the needles has a tail, and each of the ejector ends has a nose, which is coupled to the tail of one of the needles so as to push the needles out of the needle guides.

In disclosed embodiments, the device includes a needle guide holder, which is coupled to advance the needle guides from the first operative configuration to the second operative configuration and is adapted to return the needle guides to the first operative configuration after ejection of the needles. Typically, the ejector includes an actuator, which is coupled to the needle guide holder so as to be operable to eject the needles only when the needle guides are in the second operative configuration.

Additionally or alternatively the ejector is coupled to the needle guide holder so that actuation of the ejector by an operator of the device causes the needle guide holder to return the needle guides to the first operative configuration automatically, without further action by the operator. In one embodiment, the device includes first and second springs, wherein the needle guide holder is coupled to cock the first spring when the needle guides are advanced to the first operative configuration, and wherein the second spring is coupled to actuate the ejector, such that actuation of the second spring causes the first spring to be released, thereby causing the needle guide holder to return the needle guides to the first operative configuration.

In one embodiment, the device includes a handle coupled to the shaft, wherein the needle guide holder is contained in the handle, and the device includes a release actuator, which is operable to release the shaft from the handle, so as to permit replacement of the shaft.

In disclosed embodiments, the needle guides are contained inside the shaft in the first operative configuration, and the needle guides are adapted to withdraw automatically into the shaft after ejection of the needles.

Typically, ejection of the needles causes the ends of the suture thread to pass through the tissue, so that upon withdrawal of the device from the body cavity following the ejection of the needles, the suture thread tightens through the tissue while the ends of the suture thread are accessible outside the body cavity.

In some embodiments, the device includes a cannula, which is adapted to pass from a body surface through a puncture into the body cavity, the cannula having a lumen, wherein the shaft is adapted to pass through the lumen so as to access the body cavity. In one embodiment, the cannula has a distal end and includes a pliable material at the distal end, and wherein after penetrating the tissue, the needles penetrate and are captured in the pliable material.

In another embodiment, the shaft contains a lumen, which is shaped to receive a guide wire so as to permit the device to be inserted into the body cavity over the guide wire.

In yet another embodiment, the shaft contains first and second lumens having respective first and second ports disposed along the shaft at different, respective longitudinal positions, such that flow of a body fluid from the cavity through the first and second lumens is indicative of a depth of insertion of the shaft inside the body cavity.

There is also provided, in accordance with an embodiment of the present invention, a device for adjusting a depth of a cannula in a blood vessel relative to a vessel wall, the device including an elongate body, which is adapted for insertion through the cannula, the body containing first and second lumens having respective first and second distal ports and first and second proximal ports, the first and second distal ports being disposed along the body at different, respective longitudinal positions.

Typically, the depth of the device within the blood vessel is ascertainable responsively to flow of blood via the first distal port through the first lumen, while the second distal port is blocked by the vessel wall, whereby the depth of the cannula is adjusted with respect to the device.

There is additionally provided, in accordance with an embodiment of the present invention, a device for knotting a suture thread having first and second ends that have been passed through a body tissue, the device including:

a device body, having a distal end with one or more openings for receiving the ends of the suture thread after a knot has been tied in the thread;

a capture mechanism, which is contained within the body and is operative to capture the knot between the openings so as to hold the knot as the knot is tightened against the body tissue; and a blade, which is operative to cut off the ends of the suture thread while the knot is held by the capture mechanism.

In a disclosed embodiment, the device body is tubular, and the capture mechanism is mounted to slide within the tube in order to capture the knot. The device may include a spring within the device body, which is coupled to drive the blade to cut off the ends of the suture thread.

There is further provided, in accordance with an embodiment of the present invention, a method for suturing tissue adjoining a body cavity in a body of a patient, the method including:

providing a shaft having a longitudinal axis and a distal end and having first and second needle guides attached thereto in a first operative configuration in which the needle guides are parallel to the axis, the needle guides holding first and second needles, to which respective first and second ends of a suture thread are attached;

inserting the distal end of the shaft into the body cavity while the needle guides are in the first operative configuration;

deploying the needle guides outward from the distal end of the shaft into the body cavity so that the needle guides assume a second operative configuration in which the needles held by the needle guides point in a proximal direction; and ejecting the needles from the needle guides in the second operative configuration so as to cause the needles to penetrate the tissue adjoining the body cavity.

In a disclosed embodiment, the needles have respective points, and the needle guides contain the needles so that the points do not contact the tissue while the needles are held by the needle guides. The needle guides have respective outer ends, and the method includes bringing the outer ends of the needle guides in the second operative configuration into engagement with the tissue before ejecting the needles. Typically, bringing the outer ends of the needle guides into engagement with the tissue includes pulling the shaft in the proximal direction so as to create tension in the tissue by pressure of the outer ends of the needle guides against the tissue before ejecting the needles.

In disclosed embodiments, the method includes, after ejecting the needles through the tissue, pulling the shaft together with the needles and the needle guides in the proximal direction so as to remove the shaft, the needles, the needle guides and the ends of the suture thread from the body while the suture thread tightens through the tissue. Typically, inserting the distal end of the shaft includes introducing the distal end of the shaft through a puncture in the tissue, and the method includes tying the suture thread after pulling the shaft together with the needles and the needle guides in the proximal direction so as to close the puncture.

In one embodiment, introducing the distal end includes inserting the distal end of the shaft through a laparoscopic puncture port, and tying the suture thread includes closing the laparoscopic puncture port.

In another embodiment, introducing the distal end includes inserting the distal end of the shaft into a blood vessel, and tying the suture thread includes closing the puncture in a blood vessel wall. Typically, inserting the distal end of the shaft into the blood vessel includes passing the distal end of the shaft through the puncture at an oblique angle relative to the blood vessel wall, and ejecting the needles includes passing the first and second needles through the blood vessel wall at respective first and second locations that are longitudinally spaced along a length of the blood vessel, so that the suture thread, when tied, is parallel to a longitudinal axis of the blood vessel.

There is moreover provided, in accordance with an embodiment of the present invention, a method for manipulating a cannula in a blood vessel, the method including:

passing a cannula from a body surface through a puncture in the vessel wall into the blood vessel;

inserting an elongate body through the cannula, the elongate body containing first and second lumens having respective first and second distal ports disposed along the body at different, respective longitudinal positions; and adjusting a depth of insertion of the cannula in the blood vessel while observing a flow of a body fluid from the blood vessel through the first and second lumens.

In a disclosed embodiment, adjusting the depth includes positioning the elongate body so that blood flows via the first distal port through the first lumen, while the second distal port is blocked by the vessel wall, and aligning the cannula relative to the elongate body. The cannula is then positioned so that both the first and second distal ports are blocked by the cannula.

There is moreover provided, in accordance with an embodiment of the present invention, a method for suturing a body tissue, the method including:

passing first and second ends of a suture thread through the body tissue from a distal side of the tissue to a proximal side of the tissue;

pulling the first and second ends so as to tighten the suture thread against the tissue;

tying a knot between the first and second ends;

inserting the ends of the suture thread through respective openings in a capture mechanism of a knot pushing device after tying the knot, so that the knot is held between the openings;

pressing the knot pushing device toward the body tissue so as to tighten the knot against the body tissue; and releasing a blade within the knot pushing device after tightening the knot so as to cut off the ends of the suture thread while the knot is held by the capture mechanism.

The present invention will be more fully understood from the following detailed description of the embodiments thereof, taken together with the drawings in which:

BRIEF DESCRIPTION OF THE DRAWINGS

FIG. 3A is a schematic, sectional illustration showing deployment of needle guides at the distal end of a suture insertion device, in accordance with an embodiment of the present invention;

FIG. 3B is a schematic, pictorial illustration showing a detail of the distal end of the suture insertion device shown in FIG. 3A;

FIGS. 7-14 are schematic, sectional illustrations showing details of successive stages in suturing a puncture in a body cavity using a suture insertion device, in accordance with an embodiment of the present invention;

FIG. 15 is a schematic, pictorial illustration of a needle guide, in accordance with an embodiment of the present invention;

FIG. 16 is a schematic, pictorial illustration of a needle guide, in accordance with another embodiment of the present invention;

FIG. 17A is a schematic, exploded view of a needle guide, in accordance with yet another embodiment of the present invention;

FIG. 17B is a schematic, pictorial illustration showing the needle guide of FIG. 17B in its assembled configuration;

FIGS. 18A and 18B are schematic, pictorial illustrations showing elements of a needle guide in top and bottom views, respectively, in accordance with an embodiment of the present invention;

FIG. 18C is a schematic, sectional illustration showing the needle guide of FIGS. 18A and 18B in a curved configuration, in accordance with an embodiment of the present invention;

FIG. 19A is a schematic, frontal view of a suture needle, in accordance with an embodiment of the present invention;

FIGS. 19B and 19C are schematic, frontal views of a suture needle in compressed and open configurations, respectively, in accordance with an embodiment of the present invention;

FIG. 20 is a schematic, pictorial illustration of a suture needle, in accordance with another embodiment of the present invention;

FIG. 21 is a schematic, pictorial illustration showing fixation of a suture to a needle, in accordance with an embodiment of the present invention;

FIG. 22 is a schematic, pictorial illustration showing fixation of a suture to a needle, in accordance with another embodiment of the present invention;

FIG. 23 is a schematic, pictorial illustration showing details of a suture fixed to a needle, in accordance with an embodiment of the present invention;

FIGS. 24A and 24B are schematic, pictorial illustrations showing successive stages in fixation of a suture to a needle, in accordance with still another embodiment of the present invention;

FIG. 25 is a schematic, pictorial illustration of a needle ejector, in accordance with an embodiment of the present invention;

FIGS. 26A and 26B are schematic, pictorial illustrations showing details of a technique for coupling an ejector to a needle, in accordance with an embodiment of the present invention;

FIGS. 27-30 are schematic, sectional illustrations showing needle traps for capture of a suture needle in the shaft of a suture insertion device, in accordance with embodiments of the present invention;

FIG. 37A is a schematic, sectional illustration of a suture insertion device with a removable shaft, in accordance with an embodiment of the present invention;

FIGS. 37B and 37C are schematic, sectional illustrations showing details of a mechanism for connecting the shaft to the handle of the device of FIG. 37A, prior to and during removal of the shaft from the handle;

FIGS. 38A and 38B are schematic, pictorial illustrations showing the distal end of an angled suture insertion device in operation within a blood vessel, in accordance with an embodiment of the present invention;

FIG. 39A is a schematic, pictorial illustration showing the distal end of an angled suture insertion device before deployment of needle guides therefrom, in accordance with an embodiment of the present invention;

FIG. 39B is a schematic, pictorial, internal view of the suture insertion device of FIG. 39A;

FIGS. 40 and 41 are schematic, pictorial illustrations showing the angled suture insertion device of FIG. 39A in successive stages of deployment of the needle guides;

FIGS. 42-45 are schematic, detail illustrations showing couplers for attaching stabilizers to a needle guide, in accordance with embodiments of the present invention;

FIG. 50 is a schematic, pictorial illustration showing the distal end of a suture insertion device with four needle guides, in accordance with an embodiment of the present invention;

FIGS. 51 and 52 are schematic top views of suture patterns created by a suture insertion device, in accordance with embodiments of the present invention;

FIGS. 57-59 are schematic, sectional illustrations showing successive stages in the operation of the device of FIG. 56, in accordance with an embodiment of the present invention; and FIGS. 60A and 60B are schematic, sectional illustrations showing actuation and re-cocking, respectively, of a knot pushing and cutting device, in accordance with another embodiment of the present invention.

DETAILED DESCRIPTION OF EMBODIMENTS

Figure 1:
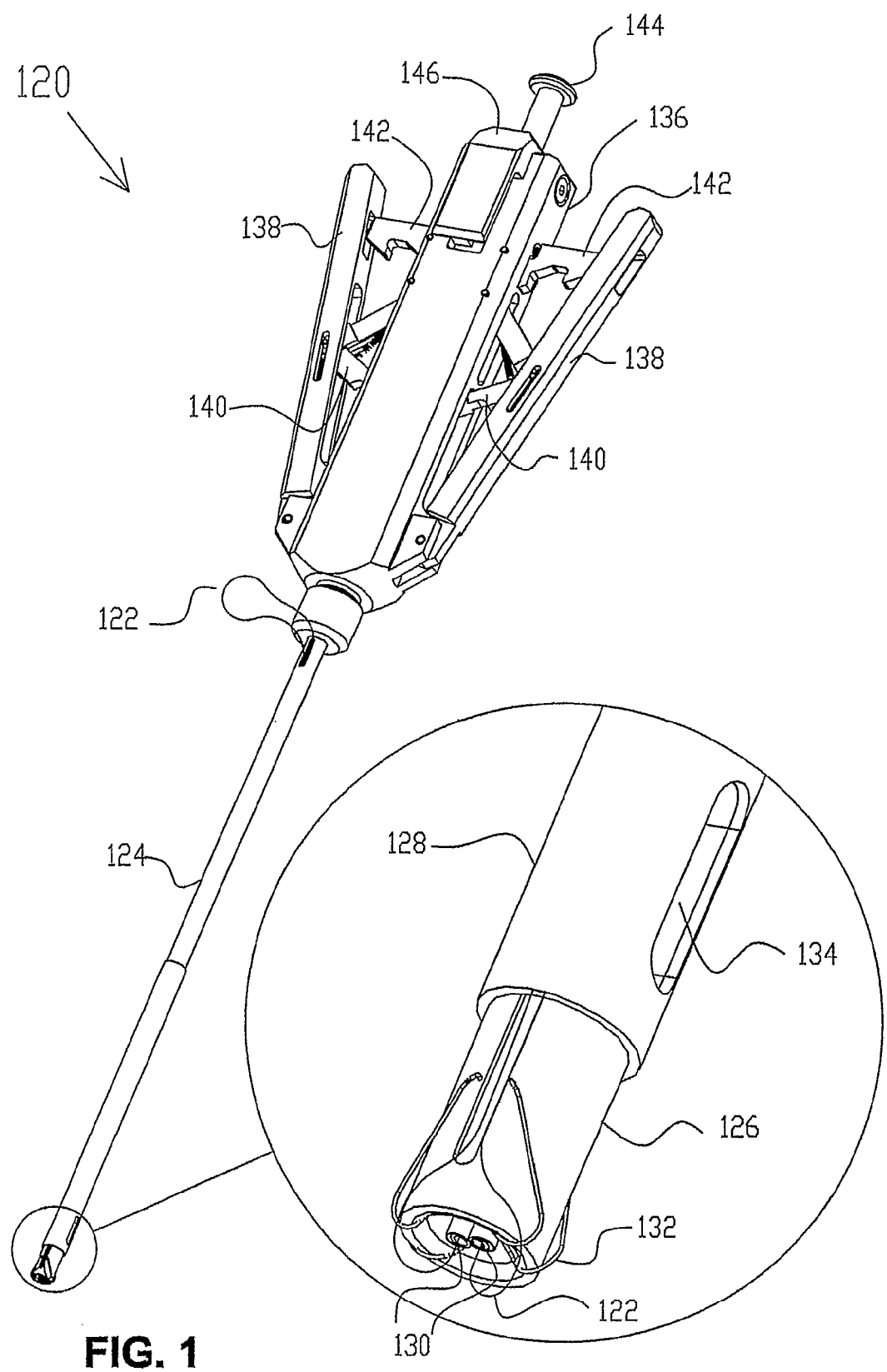
FIG. 1 is a schematic, pictorial illustration showing a suture insertion device, in accordance with an embodiment of the present invention.

FIG. 1 is a schematic, pictorial illustration showing a device 120 for insertion of a suture 122 in body tissue, in accordance with an embodiment of the present invention. Device 120 is adapted particularly for closure of laparoscopic port puncture sites in the peritoneum, following laparoscopic surgery. Devices of this sort may also be adapted, however, for closure of punctures in blood vessels following vascular catheterization, as well as other surgical operations. Some of these alternative applications and embodiments are described further hereinbelow.

Device 120 comprises a shaft 124, whose distal end is shown enlarged in the inset in FIG. 1. The device is shown in FIG. 1 in its initial, closed configuration. In this configuration, shaft 124 is inserted through the puncture, as described hereinbelow. The shaft comprises a distal tube 126, which holds needle guides 130. The needle guides comprise a resilient material, typically a superelastic material, such as Nitinol, which is formed so that when deployed (as shown below), the needle guides curve back in the proximal direction. In the initial configuration shown in FIG. 1, however, the needle guides are held straight and parallel to the axis of shaft 124 by the constraint of tube 126. Stabilizers 132 are connected to guides 130 to help maintain the guides in the desired position when the guides are deployed, as described hereinbelow.

The two ends of suture 122 are respectively connected to needles (not seen in this figure) inside guides 130. An optional outer tube 128 covers and protects the suture. The central portion of suture 122, between the ends that are connected to the needles, feeds up along shaft 124. If the suture is long enough, the middle of the suture may protrude from the proximal end of the shaft, as shown in FIG. 1. Tube 128 has side ports 134 for capturing the needles after they are ejected from guides 130.

A medical practitioner manipulates and operates device 120 using a handle 136. In order to deploy needle guides 130 once the distal end of shaft 124 is properly positioned, the practitioner squeezes hand grips 138 together. Squeezing the grips causes levers 140 to move downward (in the distal direction), thus pushing the needle guides out of tube 126. Locking hooks 142 then hold grips 138 in place against handle 136 for the duration of the operation. Once the needle guides are deployed, the practitioner presses a release button 146 to eject the needles from guides 130. Details of the guide deployment and needle ejection mechanisms are described hereinbelow.

Device 120 may be designed to be either disposable after a single use or reusable. In reusable product versions, a cocking knob 144 is used to reset the needle release mechanism after use, as described further hereinbelow. The cocking knob is not required in single-use versions.

Figure 2:
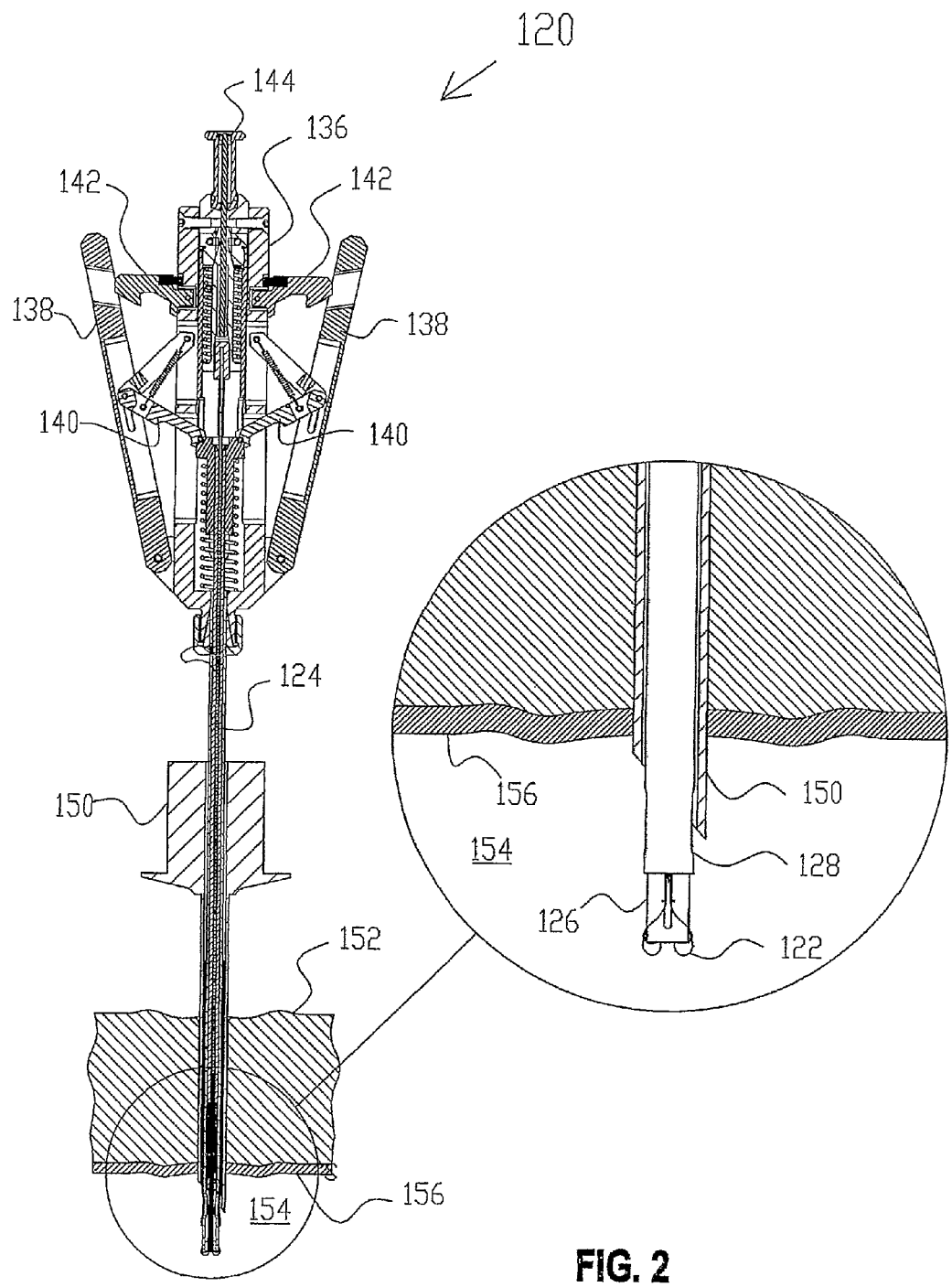
FIG. 2 is a schematic, sectional illustration showing insertion of the distal end of a suture insertion device into a body cavity, in accordance with an embodiment of the present invention.

FIG. 2 is a schematic, sectional illustration showing insertion of the distal end of suture insertion device 120 into a body cavity 154, in accordance with an embodiment of the present invention. In this example, a trocar 150 has been passed through outer tissue 152 and penetrates a wall 156 of the cavity. In the case of laparoscopic surgery, wall 156 comprises the abdominal fascia. Shaft 124 is then inserted through the working channel of trocar 150 so that the distal end of the shaft protrudes into cavity 154. Similar techniques may be used to insert the shaft of the suture insertion device into body cavities of other sorts, such as blood vessels, with different sorts of cannulae and working channels as appropriate. (The term "cannula" is used in the present patent application and in the claims to denote any and all tubes for insertion into body cavities, including—but not limited to—laparoscopic trocars and vascular sheaths.) Alternatively, in some cases, the practitioner may insert shaft 124 directly through the puncture into the body cavity, without using a cannula.

FIGS. 3A and 3B schematically illustrate deployment of needle guides 130 from the distal end of shaft 124, in accordance with an embodiment of the present invention. FIG. 3A is a schematic, sectional illustration of device 120, while FIG. 3B is a schematic, pictorial illustration showing a detail of the distal end of the device. At this stage of the procedure, the practitioner has pulled trocar 150 in the proximal direction, out of the body, so that the end of the trocar is above the area of cavity wall 156. The practitioner then squeezes grips 138 together, so that the grips are locked by hooks 142. Inward pressure of grips 138 forces levers 140 to move downward, thus pressing on a guide holder 159, which forces needle guides 130 out of the distal end of tube 126. Once deployed in this manner out of tube 126, guides 130 relax to assume their pre-formed, curved configuration.

In this configuration of guides 130, needles 160 are aimed back in the proximal direction, toward cavity wall 156. Stabilizers 132 help to maintain the relative rigidity of guides 130, so as to ensure that the needles are aimed in the proper direction. These stabilizers typically comprise metal wires or threads made from a suitable polymer or silk. The stabilizers are also useful in keeping body tissue and other objects out of the space between guides 130 and tube 126, so that needles 160 do not accidentally catch such tissues or objects when the needles are ejected. Needles 160 typically comprise a thin, elastic material, such as Nitinol. Unlike guides 130, which are produced so as to have a curved form in their relaxed state, needles 160 are straight when not geometrically constrained. Alternatively, the needles may comprise a plastic material, such as stainless steel. Although guides 130 are flexible enough to be held straight within tube 126 before they are deployed, the guides are still substantially stiffer than the needles. Therefore, the needles bend freely to assume the curvature of the guides. Ejector end pieces 162 in shaft 124 engage the rear ends of needles 160 within guides 130 in order to eject the needles from the guides, as shown in the next figure.

During insertion of shaft 124 into cavity 154 and deployment of guides 130 from the shaft, needles 160 remain completely contained within the guides. The practitioner releases the needles from the guides only after the outer ends of the guides have been brought into contact with cavity wall 156. The practitioner is typically able to verify that the ends of the guides are in contact with the wall by pulling gently outward on handle 136 and feeling the resistance as the ends of the guides press against the wall. Because the needles remain within the guides throughout this stage of the procedure, the chances that one of the needles will snag (and accidentally suture) other tissue within cavity 154 is very slight. Furthermore, because the needles are aimed to pass through wall 156 in the proximal direction, i.e., from inside cavity 154 outward, there is no danger of injury to other structures and surfaces inside the cavity. As noted above, stabilizers 132 help to prevent the needles from catching any other tissues before passing through wall 156.

Figure 4:
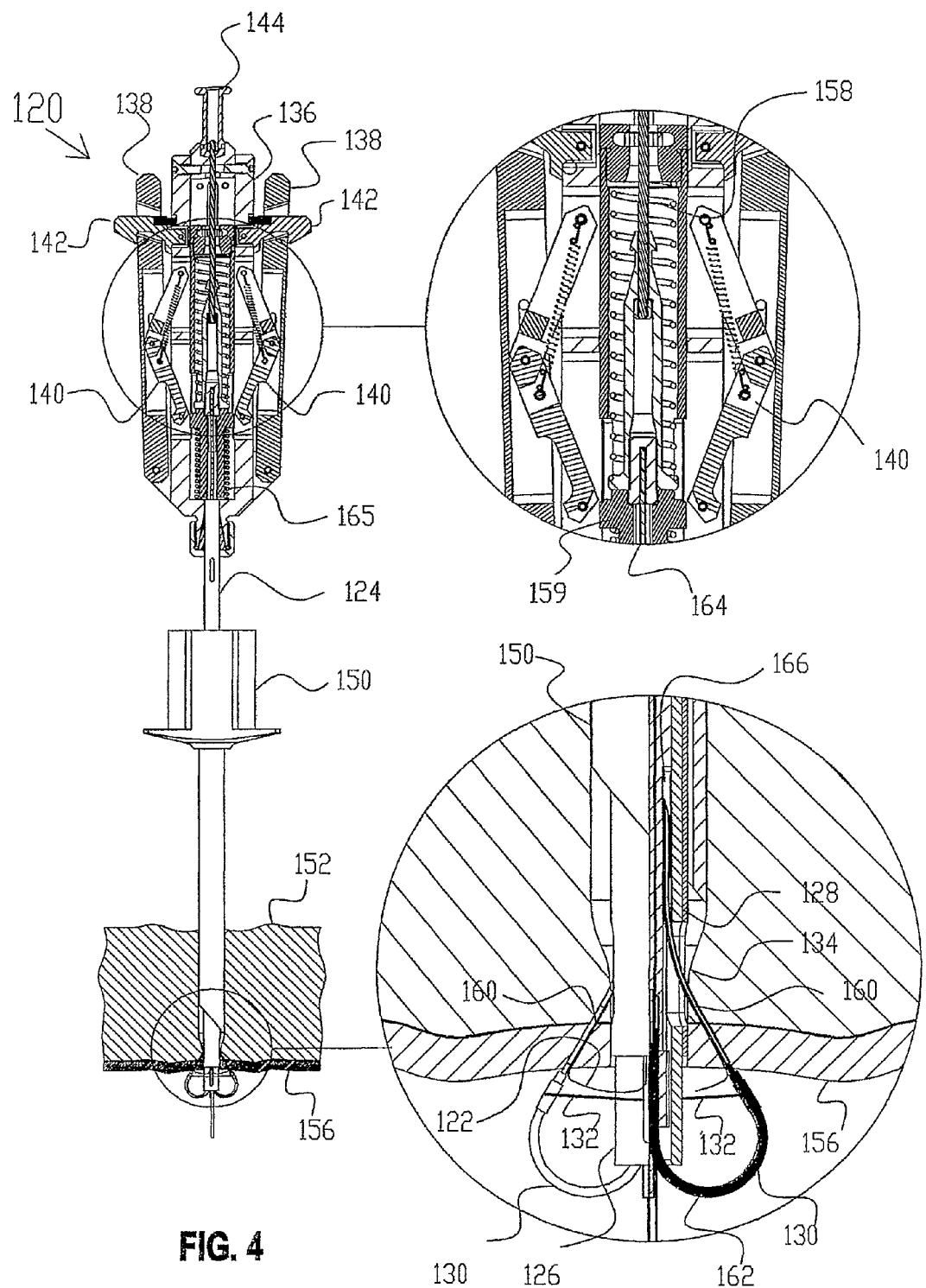
FIG. 4 is a schematic, sectional illustration showing ejection of needles from the distal end of a suture device, in accordance with an embodiment of the present invention.

FIG. 4 is a schematic, sectional illustration showing ejection of needles 160 from guides 130, in accordance with an embodiment of the present invention. Actuation of button 146 (FIG. 1) releases an ejection spring 158, which then exerts rapid downward pressure on an ejector 164. The resulting downward motion of the ejector forces end pieces 162 into guides 130, thus pushing needles 160 forward out of guides 130 and through the tissue of wall 156. The needles pull the ends of suture 122 along with them through the tissue. Typically, as shown in the figure, the end sections of guides 130 are straight, causing needles 160 to straighten immediately as they exit the guides. The end sections of the guides are aimed toward side ports 134, so that after passing through wall 156, the needles enter the side ports and are captured in a needle trap 166 within tube 126.

When grips 138 are squeezed together, levers 140 not only force guide holder 159 downward, but also compress a retraction spring 165. When ejection spring 158 is released by button 146, however, the tension holding levers 140 against guide holder 159 is also relaxed, so that the guide holder is free to move back up. Therefore, immediately after ejector 164 has ejected needles 160 from guides 130, spring 165 is released and forces guide holder 159 back upward. This reaction takes place automatically, typically within less than 0.1 sec of the actuation of button 146, and thus pulls guides 130 back into shaft 124. Further details of the mechanisms in handle 136 are described hereinbelow with reference to FIG. 33.

Figure 5:
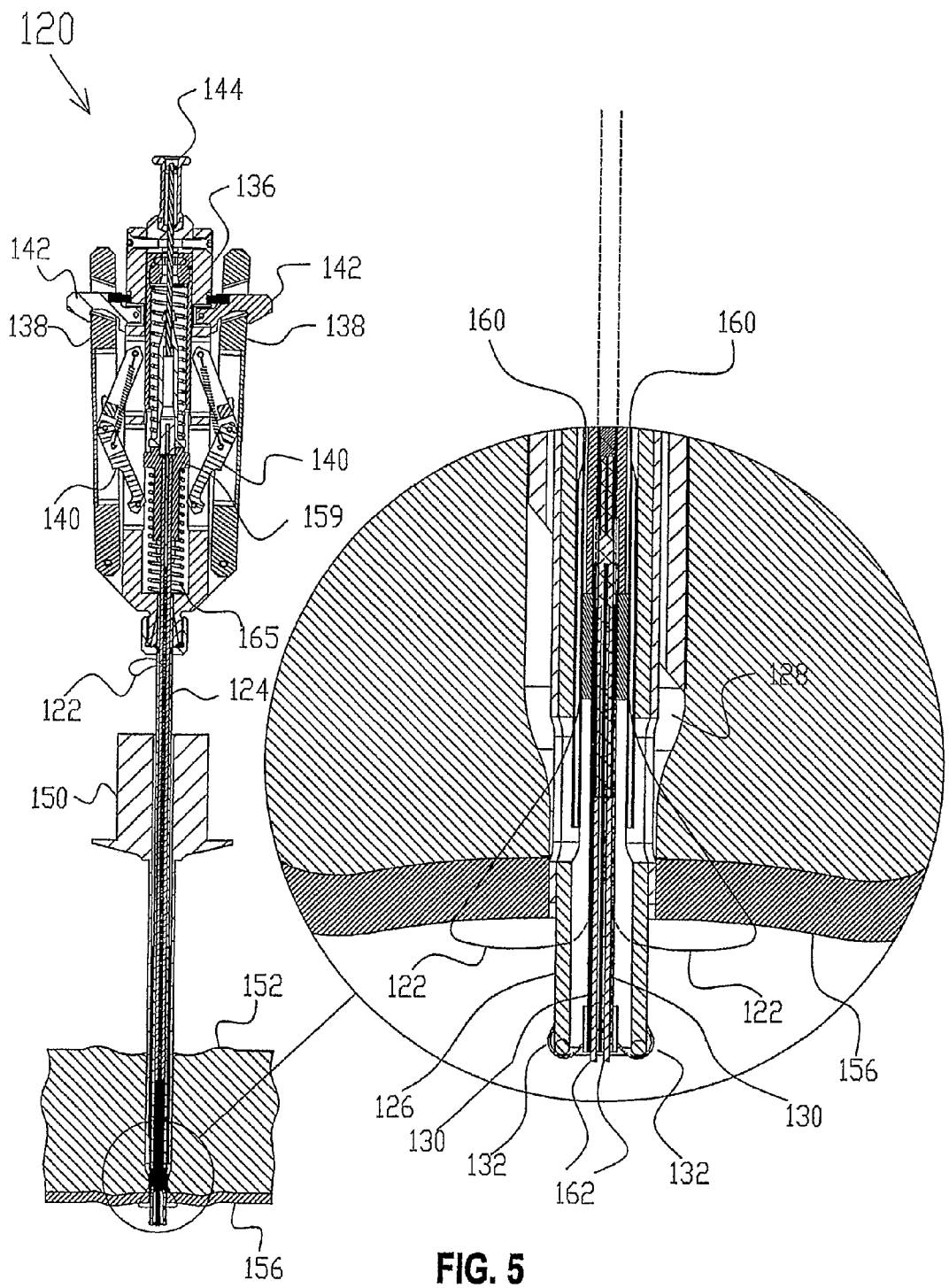
FIG. 5 is a schematic, sectional illustration showing retraction of needle guides into a suture insertion device after insertion of a suture through the wall of a body cavity, in accordance with an embodiment of the present invention.

FIG. 5 is a schematic, sectional illustration showing retraction of needle guides 130 into tube 126 after insertion of suture 122 through cavity wall 156, in accordance with an embodiment of the present invention. Retraction spring 165 has expanded, causing holder 159 to pull guides 130 back into their original, straightened configuration within tube 126. Ejector end pieces 162 remain within guides 130, while needles 160 are pulled upward within needle traps 166. The needles pull the ends of suture 122 up along with them. The practitioner pulls device 120 out through tissue 152 (typically together with trocar 150). As a result, the middle part of suture 122 feeds down along shaft 124 through the puncture in cavity wall 156, and then up through the cavity wall behind the needles.

Figure 6:
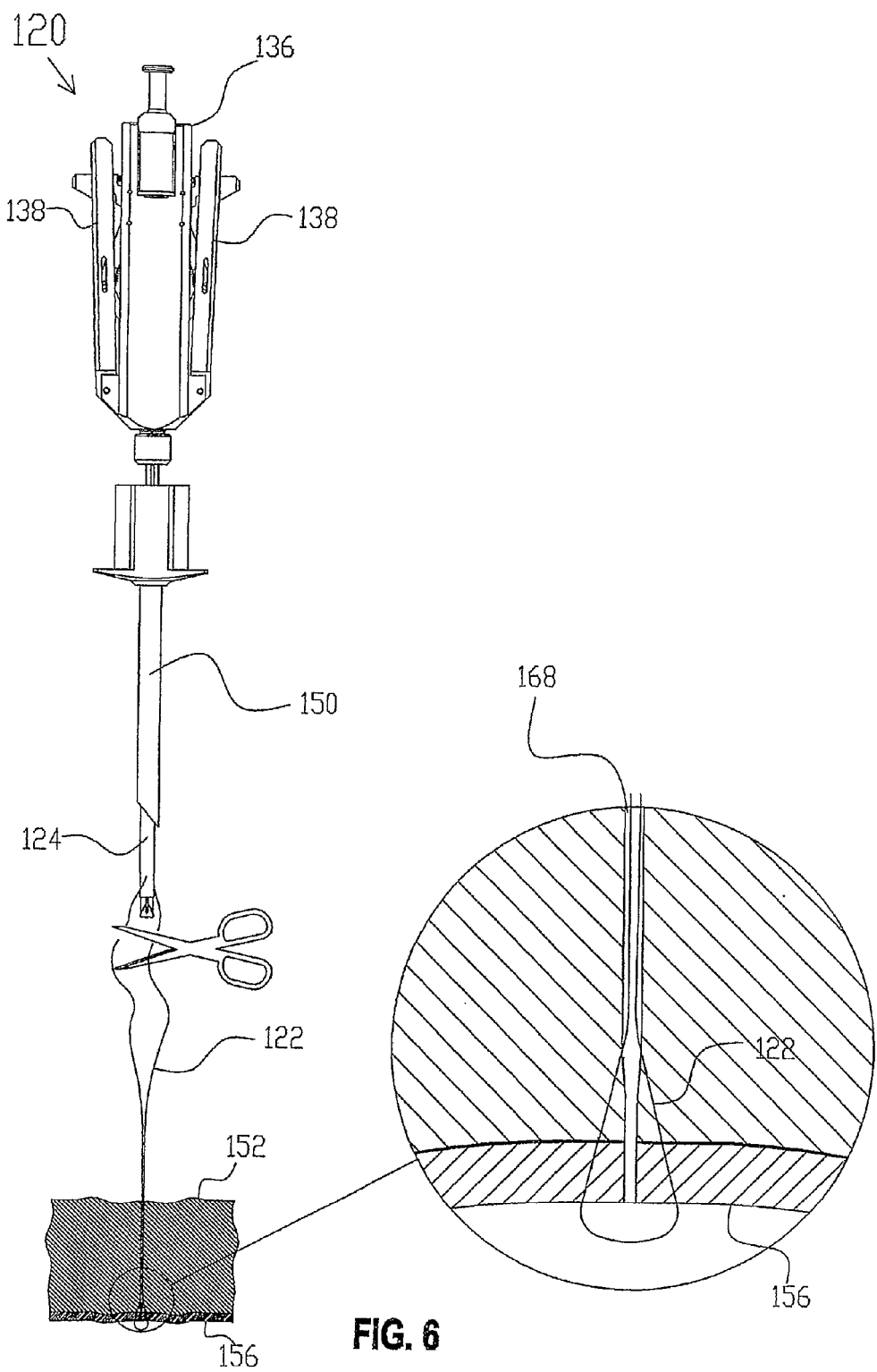
FIG. 6 is a schematic, pictorial illustration showing completion of a suture insertion operation using a suture insertion device, in accordance with an embodiment of the present invention.

FIG. 6 is a schematic, pictorial illustration showing completion of a suture insertion procedure using device 120, in accordance with an embodiment of the present invention. The entire suture 122 has fed through the holes in cavity wall 156 that were made by needles 160, and then back up through an opening 168 in the body surface at the upper end of the puncture. The suture is now snipped off from shaft 124, and is then tied to close the puncture in wall 156. The suture may be tied manually or, alternatively, using a knot pushing device, such as the devices shown in FIGS. 56-59 and in FIGS. 60A and 60B.

Figure 12:
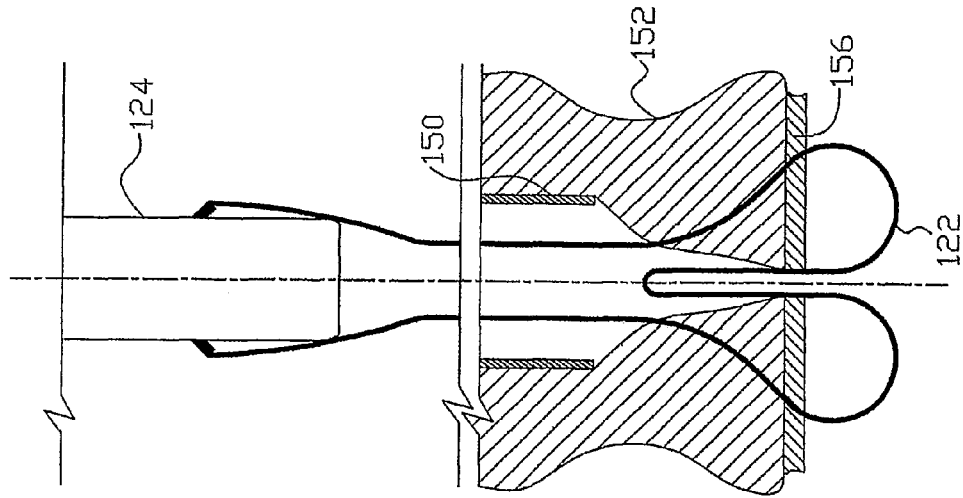

Reference is now made to FIGS. 7-14, which are schematic, sectional illustrations showing details of the suturing procedure described above, in accordance with an embodiment of the present invention. FIGS. 7-11 show the distal end of shaft 124, including needle guides 130 and needles 160, at successive stages in the procedure. Outer tube 128 is omitted from this embodiment. FIGS. 12-14 show the final stages of closure of the suture.

Figure 8:
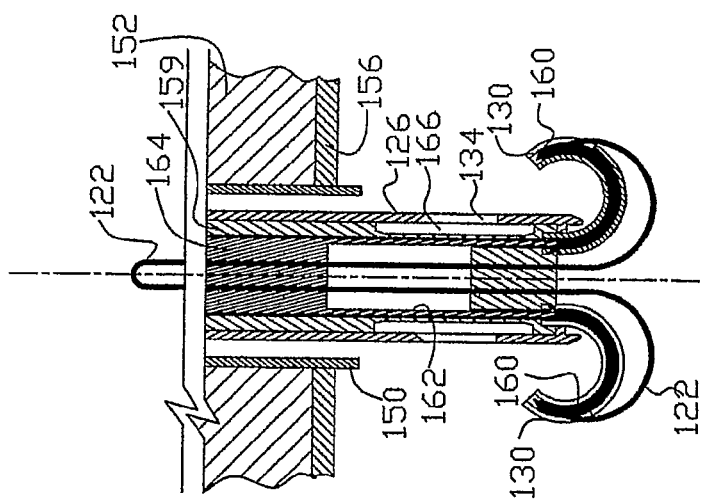
Figure 7:
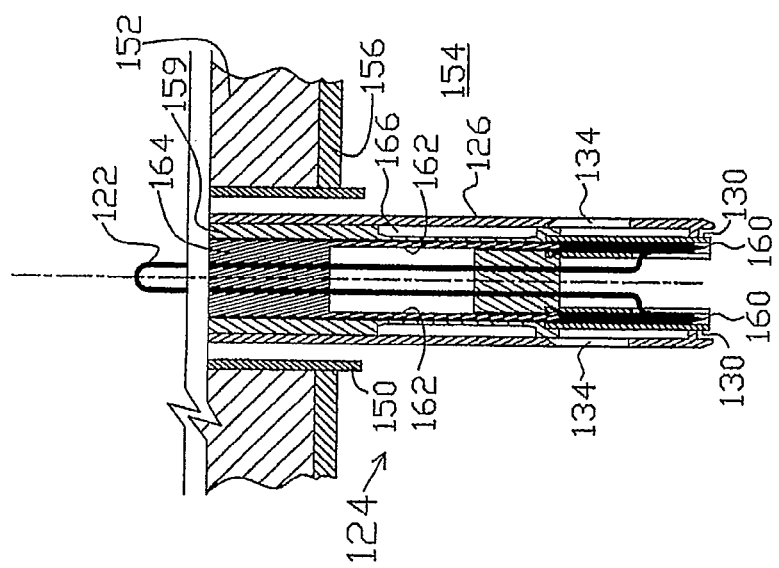

As shown in FIG. 7, during insertion of shaft 124 through trocar 150 into body cavity 154, needle guides 130 are held straight, parallel to the axis of tube 126. In the context of the disclosed embodiments of the present invention and in the claims, the terms "straight" and "parallel" do not necessarily mean that the guides are strictly straight or parallel to the axis in the geometrical sense, but rather indicate that the general orientation of the guides in this configuration runs along the axis of shaft 124. Downward movement of guide holder 159 (or equivalently, upward movement of tube 126) pushes guides 130 distally out of the end of tube 126, so that the guides are deployed in their curved configuration, as shown in FIG. 8. In this configuration, side ports 134 open into needle traps 166, in preparation for ejection of the needles. Although in FIG. 8 the distal end of device 120 is relatively far from cavity wall 156, it will be observed that guides 130 may be deployed in this manner even when the distal end of the device is nearly flush with the inner surface of the cavity wall. Device 120 is thus suitable for use even in very narrow cavities, such as blood vessels (including vessels that are partially occluded by atherosclerotic plaques).

Figure 9:
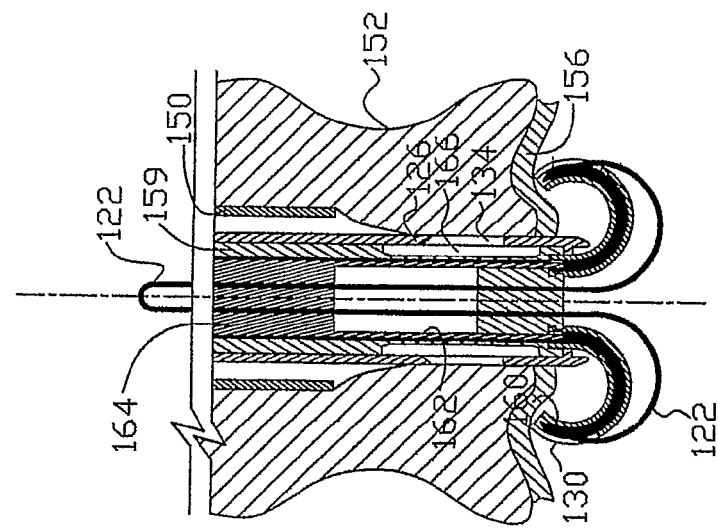
Figure 11:
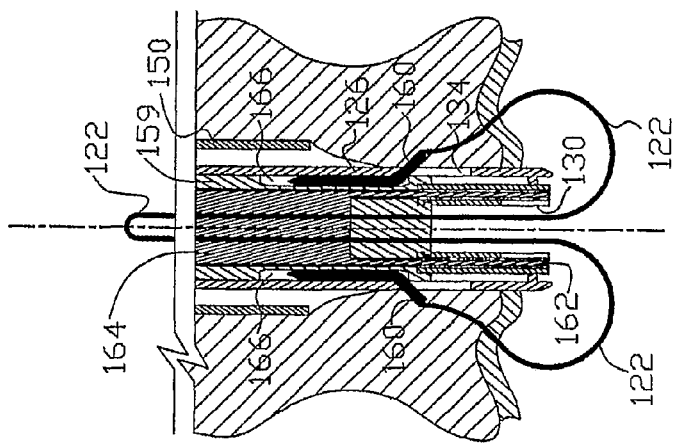
Figure 10:
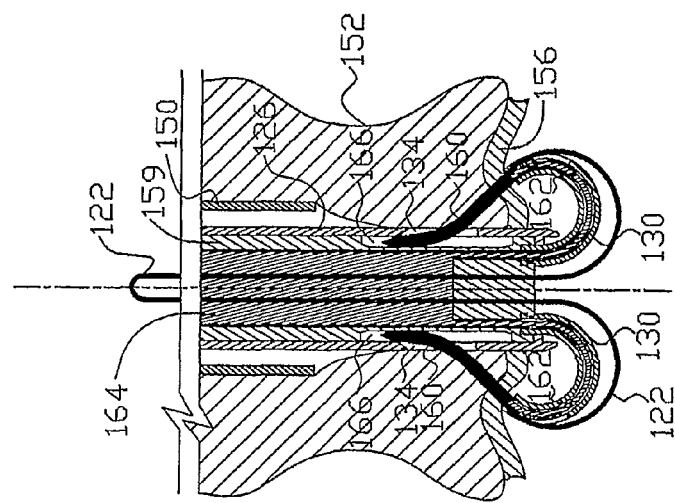

After guides 130 are deployed, but before ejecting needles 160, the practitioner pulls device 120 in the proximal direction so that the ends of guides 130 engage cavity wall 156, as shown in FIG. 9. Gently pulling the device outward in this manner deforms and creates tension in the tissue. This tension enhances the penetration of the needles through the cavity wall when the needles are subsequently ejected and also helps to ensure that a sufficient length of tissue will be captured between the tips of the two needles. The practitioner triggers the ejection mechanism (as shown in FIG. 4), causing ejector 164 to move rapidly downward, and thus pushing ejector ends 162 into guides 130, as shown in FIG. 10. As a result, needles 160 are rapidly ejected from guides 130. The needles pass straight through wall 156 into ports 134 and are captured in needle traps 166. Subsequent upward movement of guide holder 159, as shown in FIG. 11, pulls guides 130 back up into the lower end of tube 126 and may simultaneously pull needles 160 up into the needle traps, as well. The needles are pulled into the traps by friction between the needles and guide holder 159 and possibly by catching on hooks or other protrusions within traps 166, as described further hereinbelow.

Shaft 124 is then withdrawn from trocar 150 and moved up, away from the body, as shown in FIG. 12. The ends of the suture are pulled up along with the shaft, thus pulling the central part of the suture downward through the puncture in wall 156. When the entire suture has passed down through the puncture, the practitioner may pull the suture tight in order to close the puncture, as shown in FIG. 13. Immediate tensioning of the suture in this manner is useful, for example, when closing a puncture in a blood vessel following catheterization in order to reduce bleeding. The practitioner may simultaneously twist shaft 124 in order to close the puncture more tightly. The practitioner then ties a knot 170, as shown in FIG. 14, removes trocar 150, and closes the puncture at the external body surface, as well.

FIG. 15 is a schematic, pictorial illustration showing details of guide 130, in accordance with an embodiment of the present invention. The guide is typically fabricated from a tube of superelastic material, such as Nitinol, as noted above. The tube may have substantially any suitable profile, such as a circular profile, an elliptical profile, or a rectangular or oblong profile. Tubes of this sort are available, for example, from Johnson Matthey Inc. (San Jose, Calif.). Non-circular profiles are advantageous in that they may force needle 160 to maintain a desired orientation (assuming the needle profile to be non-circular), and they may also provide greater stability against sideways bending of the guides.

A central portion 176 of the tube is then set (or "trained") to assume a curved shape in its austenitic state, as shown in FIG. 15, while end sections 172 and 174 are held straight. Methods for "training" Nitinol in this manner are known in the art. Typically, the tube is placed in a mandrel of the desired shape and is then heated to a high temperature (typically 500° C. for at least 5 min) and cooled thereafter. Guides 130 may be formed in this way with a bend angle slightly smaller than the actual, desired bend angle that the guides are to assume when deployed. This technique can be used to create a certain preload tension in stabilizers 132 when the guides are deployed (FIG. 3B), thus enhancing the stability of the deployed guides.

FIG. 16 is a schematic, pictorial illustration of needle guide 130, in accordance with another embodiment of the present invention. This embodiment is similar to that shown in FIG. 15, with the addition of a slot 178 at the outer end of the guide. Slot 178 can be used to accommodate the end of suture 122, in order to reduce the likelihood that the suture sill snag on other parts of device 120 or on body structures in cavity 154.

FIGS. 17A and 17B are schematic, pictorial illustrations of a needle guide 180, in accordance with yet another embodiment of the present invention. FIG. 17A is an exploded view showing the parts of the needle guide, while FIG. 17B shows the needle guide in its assembled configuration. Needle guide 180 in this embodiment is made from a plate 182 of Nitinol, which is trained to shape in the manner described above. Needle 160 is held in place against plate 182 by a collar, which may be formed, for example, from two sections 184 that are fastened together over the end of the plate. Typically, sections 184 comprise a suitable metal, such as stainless steel or titanium, and are welded together over plate 182, using laser welding or another suitable technique. One or more additional sleeves (not shown) may be fastened over plate 182 at other locations in order to prevent sideward movement of the needle.

Reference is now made to FIGS. 18A, 18B and 18C, which schematically illustrates a needle guide 185, in accordance with still another embodiment of the present invention. FIGS. 18A and 18B are top and bottom views, respectively, of needle guide 185 in the straight configuration in which the needle guide is held within shaft 124, while FIG. 18C is a sectional view through the needle guide in its curved configuration. (The terms "top" and "bottom" here refer to the perspective of FIG. 18C.) Needle guide 185 comprises a plate 186 and a cover 187, both of which are typically made of Nitinol. A slot is cut in plate 186 to accommodate needle 160. This configuration permits the use of a relatively thick, strong needle while still bending to a small radius of curvature, as shown in FIG. 18C. Plate 186 and cover 187 are trained to this shape in the manner described above.

As shown in FIG. 18B, cover 187 is secured to plate 186 by protrusions 188, which fit into slots 189 in the plate. The protrusions are fixed in place by pins 191. As can be seen in the figure, the more distal slots are longer than the corresponding protrusions, thus permitting cover 187 to shift longitudinally relative to plate 186 when guide 185 bends. The relative movement is helpful in relieving strains that might otherwise lead to material failure.

FIG. 19A is a schematic, frontal view of needle 160, in accordance with an embodiment of the present invention. In this embodiment, needle 160 is cut from a flat sheet of metal, typically a superelastic metal such as Nitinol. (Alternatively, in other embodiments, as shown below, needle 160 may be produced from a tube or rod, which may have a circular or elliptical profile.) Needle 160 may be cut using a laser or a suitable die, as is known in the art. As noted earlier, the needle is produced so that in its relaxed, austenitic state, the needle is straight, but because the needle is made from thinner, more flexible material than guide 130, the needle bends with the guide when the guide is deployed. An eye 190 is also cut in the needle to accommodate suture 122. Optionally, protrusions 192 are formed on the shank of needle 160 in order to catch on the inner sides of needle trap 166, thereby holding the needle more securely in the trap as shaft 24 is withdrawn from the body. The pointed tip of needle 160 may also be ground down to a sharper point, in order to facilitate passage of the needle through cavity wall 156.

It is possible and desirable to make needles 160 very thin and flexible. The shape and aim direction of the needles is determined by guides 130, which are relatively stiff and stable, rather than by the needles themselves. Thin needles are able to pass through cavity wall 156 more easily, with less tissue trauma and ancillary bleeding, than are the thicker, stiffer needles that are used in suturing devices known in the art.

FIGS. 19B and 19C are schematic, frontal views of a suture needle 194 in compressed and open configurations, respectively, in accordance with another embodiment of the present invention. Needle 194 is similar to needle 160, as shown in FIG. 19A, with the addition of a resilient expanding section 196. The needle is cut from a sheet of elastic material in the shape shown in FIG. 19B. Inside guide 130, however, section 196 is compressed into the shape shown in FIG. 19C. When the needle is ejected from the guide, section 196 opens outward, so that protrusions 192 on section 196 help to secure the needle within needle trap 166.

FIG. 20 is a schematic, pictorial illustration of a suture needle 200, in accordance with yet another embodiment of the present invention. Needle 200 has an elastic protrusion 204, which is typically formed by cutting and then applying appropriate heat treatment to the needle material. Protrusion 204 is used to secure needle 200 in a needle trap by catching on a suitable hook in the needle trap (as shown below in FIG. 29). Needle 200 may also have a narrow tail 202, to facilitate coupling of the needle to ejector end piece 162 (as shown below in FIGS. 26A and 26B). Although the needles shown in this figure and in the preceding figures each have a certain combination of features, these combinations have been chosen solely for the sake of illustration. Other combinations of these features, or similar features, will be apparent to those skilled in the art.

FIG. 21 is a schematic, pictorial illustration showing fixation of suture 122 to needle 160, in accordance with an embodiment of the present invention. Suture 122 is fed through eye 190, and is then heated to form a bulb 210, which holds the suture in place. This technique is suitable particularly for polypropylene sutures, but it may also be used with polymer sutures of other types. A similar sort of bulb may be formed from a suitable biocompatible adhesive, such as Loctite Hysol® M-31CL epoxy, and this fixation technique may thus also be used with other types of sutures, such as silk.

FIG. 22 is a schematic, pictorial illustration showing fixation of suture 122 to a needle 212, in accordance with another embodiment of the present invention. Needle 212 in this case is tubular and may be made, for example, from a tube of superelastic material, such as Nitinol. Suture 122 is fed in through the pointed front end 214 of the needle. The suture may then be glued in place using a suitable biocompatible adhesive, such as the above-mentioned Hysol epoxy. Alternatively or additionally, the end of the suture may be fed through to the rear end of the needle and then heat treated to form a bulb 216.

FIG. 23 is a schematic, pictorial illustration showing details of suture 122 fixed to needle 212, in accordance with an embodiment of the present invention. This embodiment addresses the problem that the suture itself may be too thick to fit inside the lumen of the tubular needle. Therefore, suture 122 in this embodiment is made up of a short, thin end section 216, which is coupled to a thicker main section 217 by a coupler 218. Section 216 may comprise a metal wire, such as a braided stainless steel wire, which may be glued or otherwise fixed inside needle 212, as described above. Section 217 typically comprises a polymer, such as a polymer that gradually dissolves inside the body (for example, Ethicon Monocryl® or Vicryl®), as is known in the art. Sections 216 and 217 may be joined to connector 218 by pressure crimping, glue, welding, or any other suitable means known in the art.

Other methods for producing suture 122 with narrow end sections will be apparent to those skilled in the art. For example, the ends of a polymer suture may be heated and drawn to a smaller diameter. As another example, if the suture comprises a core with a braided exterior over the core, the exterior braiding may be removed from the ends of the suture to narrow their diameter. One advantage of using a thick suture, of comparable diameter to that of needle 212, is that the suture then completely fills the trace that the needle makes through cavity wall 156, thus sealing and reducing leakage through the trace.

FIGS. 24A and 24B are schematic, pictorial illustrations showing successive stages in fixation of suture 122 to a flat needle 220, in accordance with still another embodiment of the present invention. Needle 220 is cut from a sheet of elastic material, and an eye having the form of a slot 222 is cut through the needle near the pointed tip. To insert suture 122, slot 222 is pulled open, as shown in FIG. 24A, and the end of the suture is fed into the open slot. The slot is then released, so that it clamps shut, holding the suture in place, as shown in FIG. 24B.

In the embodiments shown above, ejector 164 and ejector end pieces 162 are formed from a single piece of material, which may be a metal, such as stainless steel or Nitinol, or a suitable plastic. Typically, ejector 164 comprises a rod or tube, whose distal end is cut to form the end pieces, typically by laser cutting or fine machining. Alternatively, the ejector may be formed by injection molding. As noted earlier, end pieces 162 are made sufficiently thin and flexible so that they can advance freely into guides 130 while the guides are deployed in their curved configuration.

FIG. 25 is a schematic, pictorial illustration of an ejector 230, in accordance with an alternative embodiment of the present invention. In this embodiment, ejector comprises an ejector body 232 and separate end pieces 234, which are fixed to body 232. The end pieces may be fixed to the body by any suitable means, such as crimping, glue, laser welding or a coupling pin (not shown). End pieces 234 may comprise, for example, two parallel strips fixed together, or a single strip, wire or tube that is bent in the middle. Alternatively, the end pieces may be cut out in an elongated U-shape from a metal plate, by laser cutting, for example. In this case, the two end pieces may be made to bow slightly outward for greater mechanical strength during ejection of needles 160 from guides 130. Other arrangements of end pieces 234 will be apparent to those skilled in the art.

FIGS. 26A and 26B are schematic, pictorial illustrations showing details of a technique for coupling ejector end piece 162 to needle 160, in accordance with an embodiment of the present invention. Needle 160 ends in tail 202, as described above with reference to FIG. 20. End piece 162 has a matching tip 235. A connector 236 fits over and holds tail 202 and tip 235 together. This arrangement ensures secure, positive engagement between the ejector end piece and the needle during ejection. Typically, connector 236 is securely fastened to tip 235 but not to tail 202, so that needle 160 is freed from the connection after the needle is ejected, while connector 236 remains attached to the ejector end piece inside guide 130.

FIGS. 27-30 are schematic, sectional illustrations showing different arrangements of needle trap 166, in accordance with embodiments of the present invention. The figures show needle 160 and trap 166 in the situation illustrated in FIG. 11, in which guide holder 159 and guides 130 have been withdrawn upward inside tube 126, and the needle is captured in the trap. In the embodiment shown in FIG. 27, needle 160 has been drawn completely inside trap 166, along with the end of suture 122 that is attached to the needle. As noted earlier, friction between the needle and the guide holder tends to draw the needle upward into the trap. Alternatively, as shown in FIG. 28, the entry to trap 166 may be sufficiently narrow and geometrically bent so that needle 160 lodges in the entry when the needle is ejected from guide 130. The needle may also include a bend point introduced at the time of manufacture, so that the needle bends and lodges in the desired position. The needle may remain stuck in this position when guide holder 159 moves upward, or alternatively, the needle may be drawn part way into trap 166 by the movement of the guide holder. In any of these embodiments, protrusions 192 on the shank of the needle (as illustrated in FIGS. 18 and 19A) may assist in holding the needle securely inside the trap.

FIG. 29 shows a needle trap with a hook 240, for use with needles of the type of needle 200 (FIG. 20). When the needle enters trap 166, protrusion 204 catches on hook 240, and thus prevents the needle from sliding back out of the trap.

In FIG. 30, tube 126 is surrounded by a collar 242 made of a pliable material, typically a suitable elastomer, such as silicone. Trap 166 is defined by port 134 in the outer surface of tube 126, which is covered by collar 242, Needle 160 passes through the collar and is held in place by pressure of the collar against the tube. Protrusions 192 on the shank of the needle may help to hold the needle more securely in the trap. In this case, the needle is captured securely irrespective of the upward movement of guide holder 159. Alternatively, a pliable collar may be placed over port 134 for use in conjunction with other types of traps, such as that shown in FIG. 28.

Figure 31A:
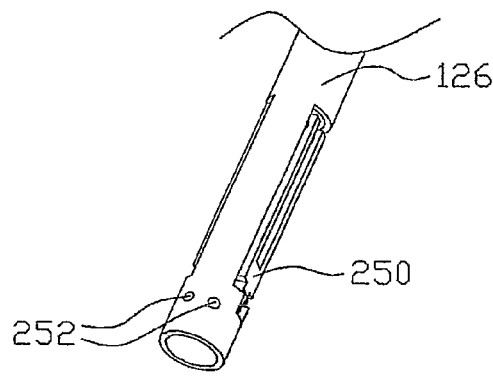
FIGS. 31A and 31B are schematic, pictorial illustrations showing details of needle guides and stabilizing struts for the needle guides at the distal end of a suture insertion device, before and during deployment of the needle guides, in accordance with an embodiment of the present invention.
Figure 31B:
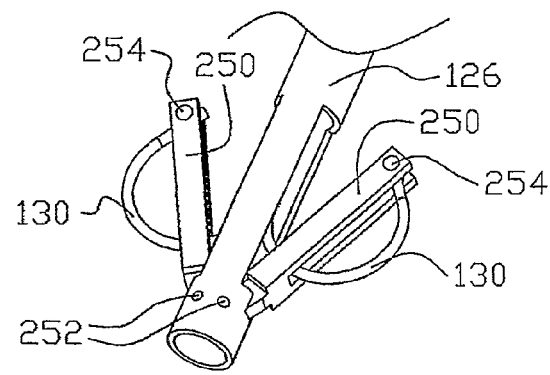

FIGS. 31A and 31B are schematic, pictorial illustrations showing details of stabilizer struts 250 for needle guides 130, in accordance with an alternative embodiment of the present invention. Although stabilizers 132 (FIG. 3B) provide good control of the positions of guides 130 in the radial direction, they still permit some transverse movement. Struts 250, on the other hand, are stiff enough to give complete control over the movement of guides in all directions. The struts are connected at one end to tube 126 by hinges 252, and at the other end by hinges 254 to guides 130. During insertion and removal of the suture insertion device from the body, struts 250 and guides 130 are closed inside tube 126, as shown in FIG. 31A. The struts and guides are deployed outward, as shown in FIG. 31B, prior to ejection of the needles.

Figure 32A:
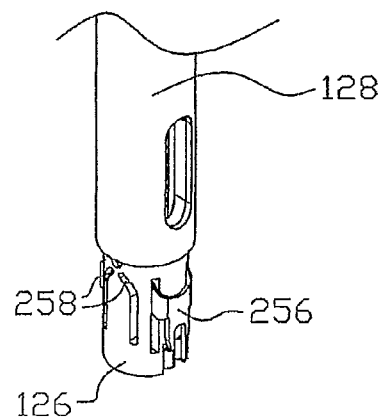
FIGS. 32A and 32B are schematic, pictorial illustrations showing details of needle guides and stabilizing struts for the needle guides at the distal end of a suture insertion device, before and after deployment of the needle guides, in accordance with another embodiment of the present invention.
Figure 32B:
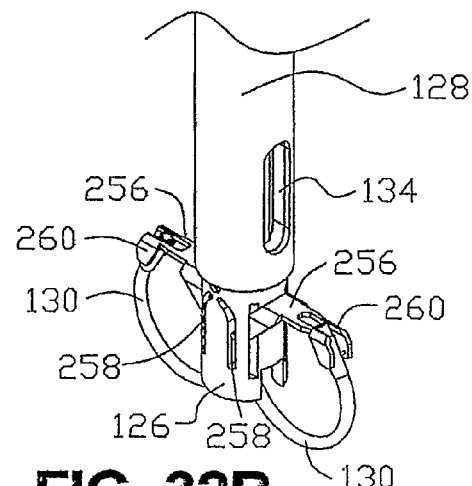

FIGS. 32A and 32B are schematic, pictorial illustrations showing details of stabilizer struts 256 for needle guides 130, in accordance with another embodiment of the present invention. In this embodiment, unlike the embodiment of FIGS. 31A and 31B, guides 130 are deployed out of the distal end of tube 126. To accommodate this arrangement, struts 256 are attached by a sliding hinge 238 to tube 126. The struts are attached at their outer ends to guides 130 by fixed hinges 260.

Figure 33:
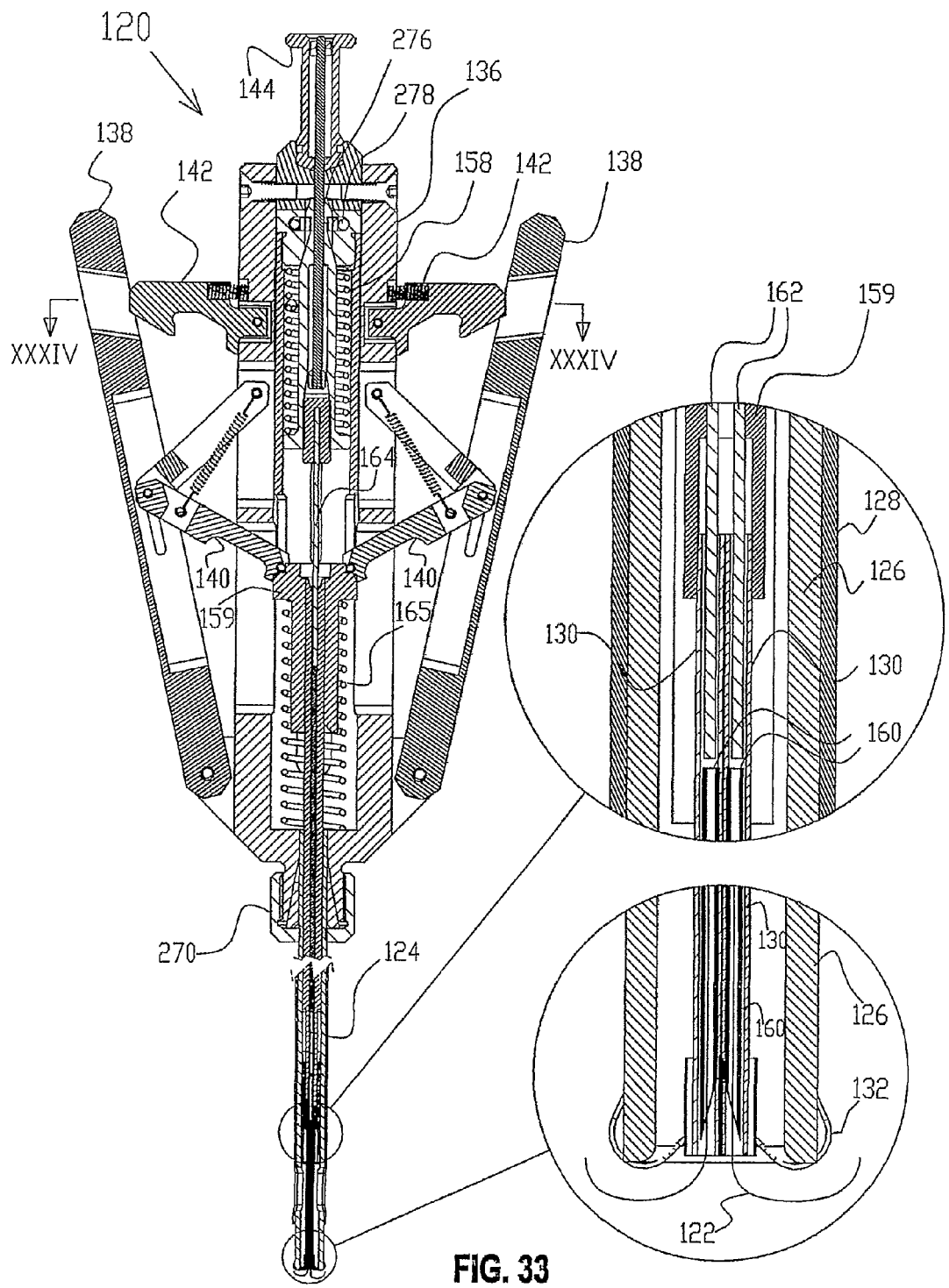
FIG. 33 is a schematic, sectional illustration showing details of mechanisms in a suture insertion device, in accordance with an embodiment of the present invention.

FIG. 33 is a schematic, sectional illustration showing details of the mechanisms in handle 136 and shaft 124 of device 120, in accordance with an embodiment of the present invention. Device 120 is shown here in its initial state (as in FIG. 2), wherein ejection spring 158 is cocked and retraction spring 165 is relaxed. Levers 140 engage guide holder 159, but both guide holder 159 and ejector 164 remain in their initial, elevated positions, such that guides 130 are held inside tube 126 and needles 160 are contained within guides 130. The elements within handle 136 are held in place by a locking nut 270 with a conical fitting.

Prior to ejection of needles 160, an ejector head 276, at the upper end of ejector 164, is held in place by a clip 278. Since head 276 is firmly fixed to ejector 164, the ejector cannot eject needles 160 from guides 130 until clip 278 is released by actuation of release button 146 (FIG. 1). The release button, however, is not aligned with clip 278 until grips 138 have been closed. Closing the grips causes levers 140 to lower guide holder 159, and with it to lower ejector 164 and head 276. This is the situation shown in FIGS. 3A and 3B, in which guides 130 have been deployed from tube 126. Lowering holder 159 in this manner aligns release button 146 with clip 278, as well as compressing retractor spring 165, as noted above.

Figure 34:
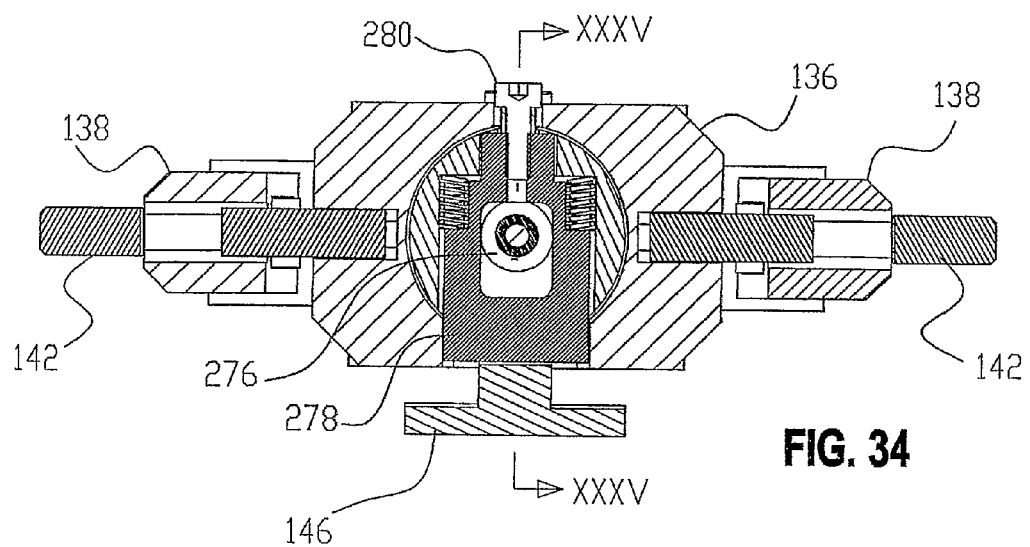
FIG. 34 is a schematic, cross-sectional illustration of the suture insertion device of FIG. 33, taken along a line XXXIV-XXXIV in FIG. 33.
Figure 35:
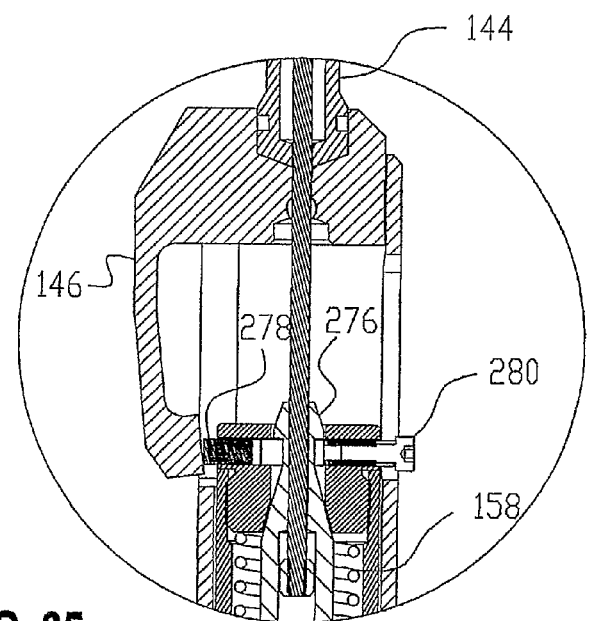
FIG. 35 is a schematic, cross-sectional detail illustration of the suture insertion device of FIG. 33, taken along a line XXXV-XXXV in FIG. 34.

FIGS. 34 and 35 are schematic, cross-sectional illustrations of device 120, showing details of the operation of release button 146, in accordance with an embodiment of the present invention. The cross-section in FIG. 34 is taken along a line XXXIV-XXXIV in FIG. 33 (except that FIG. 34 shows device 120 in the configuration of FIG. 3A, in which grips 138 have already been closed and locked by hooks 142). The cross-section shown in FIG. 35 is taken along a line XXXV-XXXV in FIG. 34.

As shown in FIG. 34, clip 278 is spring-loaded against a pin 280, which slides up and down with head 276. As long as ejector head 276 is in the upper position shown in FIG. 33, button 146 does not contact clip 278, and therefore, the ejector head cannot be released from the clip. Ejector spring 158 therefore remains cocked, and needles 160 remain within guides 130. Thus, there is no danger that the needles will be ejected from the guides (in the distal direction) before the guides are fully deployed.

When grips 138 are squeezed together, ejector head 276 and clip 278 are lowered to the position shown in FIG. 35. Now, when the practitioner presses button 146, clip 278 is pushed inward along pin 280, so that head 276 is released from the clip. As a result, spring 158 is fee to expand, driving ejector 164 downward (FIG. 4) so as to eject needles 160. The subsequent automatic release of retraction spring 165 (FIG. 5), by disengagement of the ends of levers 140 from guide holder 159, causes the guide holder to retract guides 130 into tube 126, thus completing the process.

Figure 36A:
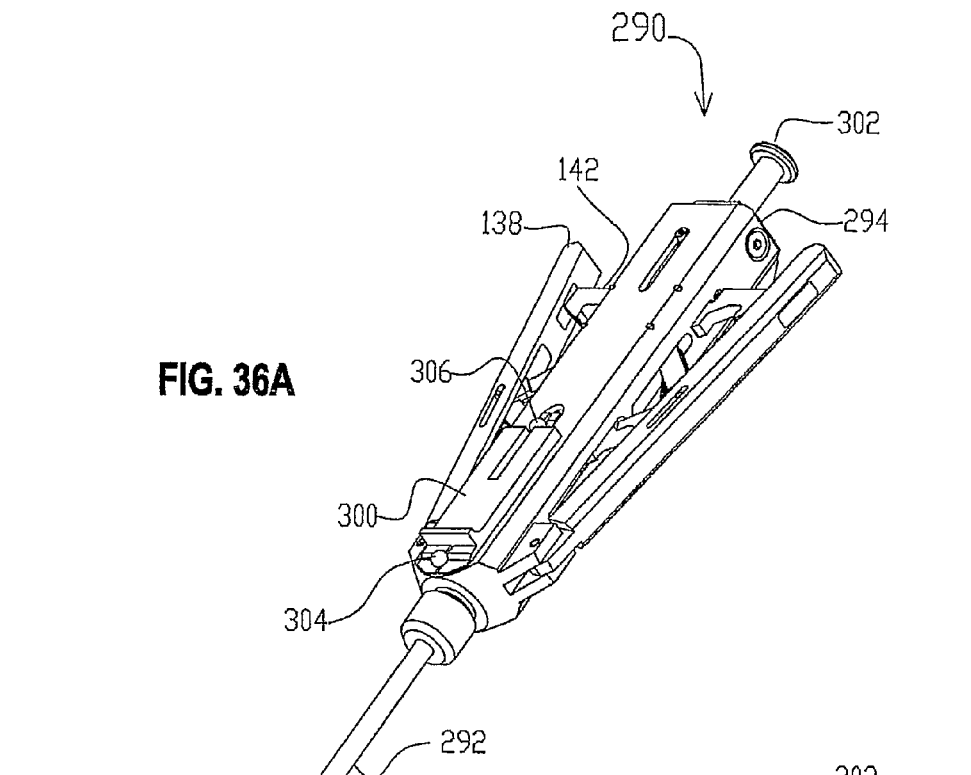
FIG. 36A is a schematic, pictorial illustration of a suture insertion device with a removable shaft, in accordance with an embodiment of the present invention.
Figure 36B:
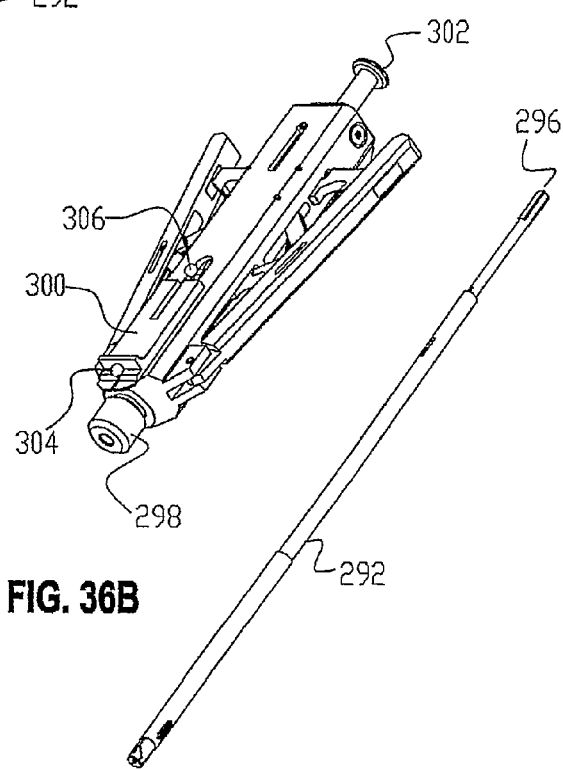
FIG. 36B is a schematic, pictorial illustration showing the separate shaft and handle, respectively, of the suture insertion device of FIG. 36A.

FIGS. 36A-36B are schematic, pictorial illustrations of a suture insertion device 290 with a removable shaft 292, in accordance with an alternative embodiment of the present invention. FIG. 36A shows the device in its operational configuration, with shaft 292 and a handle 294 fitted together. FIG. 36B shows the separate shaft 292 and handle 294, respectively. Operation of device 290 is identical to that of device 20, except for the added facilities in device 290 for replacing the shaft and reusing the handle. Typically, the shaft is suitable for only a single use, and is then disposed of, because the operation of loading needles 160 into guides 130 is most conveniently performed in the manufacturing plant. Therefore, device 120, with integral shaft 124, can be used only once. On the other hand, handle 294 can be reused multiple times, by performing suitable sterilization and replacing shaft 292 after each use.

As shown in FIG. 36B, shaft 292 comprises a proximal fitting 296, for mating with the mechanisms of guide holder 159 and ejector 164 inside handle 294. Fitting 296 fits into a receptacle 298 in the handle and is held in place by locking pins 304 and 306. A release actuator 300 is used to release these pins when the shaft is to be replaced. (The release mechanism is shown in greater detail below in FIGS. 37A, 37B and 37C.) In preparation for reuse, the practitioner or other operator releases hooks 142 to open grips 138 and pulls up on a knob 302 to re-cock ejection spring 158. A new shaft 292 is then fitted into receptacle 298; and device 290 is ready for reuse.

FIGS. 37A-37C are schematic, sectional illustrations of suture insertion device 290, in accordance with an embodiment of the present invention. FIG. 37A provides an overview of the device, while FIGS. 37B and 37C show details of the mechanism used for connecting shaft 292 to handle 294. In FIG. 37B, shaft 292 is connected to handle 294 and ready for operation. Pin 304 engages tube 126 of shaft 292, while pin 306 engages guide holder 159 to enable deployment of the needle guides. To release pins 304 and 306, as shown in FIG. 37C, release actuator 300 is pushed downward, causing diagonal sections 308 to slide under the heads of the pins. This action pulls the pins outward, away from shaft 292, and thus releases the shaft from the handle.

In an alternative embodiment, not shown in the figures, device 120 (FIG. 1) may be reused in its entirety multiple times. For this purpose, after each use, the operator releases hooks 142 to open grips 138 and pulls up on a knob 144 to re-cock ejection spring 158. The operator then inserts a new pair of suture needles, with a suture connected between them, into guides 130. After sterilization, the device is ready for reuse.

FIGS. 38A and 38B are schematic, pictorial illustrations showing the distal end of an angled suture insertion device 324 in operation within a blood vessel 320, in accordance with an embodiment of the present invention. Although in the preceding embodiments, device 120 was inserted straight through tissue through wall 156 of cavity 154 (as is typical, for example, in laparoscopic surgery), the principles of that device may be adapted, with certain modifications, for closing diagonal punctures as are commonly used in vascular catheterization procedures. This sort of adaptation is shown in FIGS. 38A and 38B and the figures that follow.

In the scenario shown in FIG. 38A, a cannula 326 (also referred to as a sheath) has been inserted through a wall 322 of blood vessel 320. Vessel 320 may be the femoral artery, for example, or substantially any other blood vessel large enough to accommodate cannula 326 and device 324. After completion of a catheterization procedure, the catheter (not shown) is withdrawn from cannula 326, and device 324 is inserted in its stead. Guides 328 are then deployed from the shaft of device 324, in the manner described above. After deploying the guides, the practitioner withdraws cannula 326, as shown in FIG. 38B, and pulls device 324 outward until the ends of guides 328 engage wall 322. The needles are then ejected from the guides through wall 322, and suture 122 is tied in place. The course of the procedure follows the steps described above with reference to FIGS. 7-14.

It can be seen in FIGS. 38A and 38B that guides 328 are non-symmetrical, i.e., the guides have different lengths and curvatures to accord with the angled entry of cannula 326 into vessel 320. This arrangement permits suture 122 to be inserted through vessel wall 322 along the longitudinal axis of the vessel. This feature of the present embodiment is important because the puncture in the blood vessel wall typically cuts the wall in a peripheral direction. A longitudinal suture is generally most effective against subsequent peripheral tearing of the vessel wall along the puncture line. The configuration of guides 328 also permits the needles to penetrate wall 322 at points that are relatively far apart, so that the suture captures a substantial length of the wall tissue.

FIGS. 39A and 39B are schematic, pictorial illustrations showing the distal end of suture insertion device 324 before deployment of needle guides 328, in accordance with an embodiment of the present invention. FIG. 39A is an external view of device 324, wherein the needle guides are covered by an outer tube 336, while FIG. 39B show an internal view of device 324, with tube 336 removed. Suture 122 is omitted from these figures and the subsequent figures for the sake of simplicity.

Because of the non-symmetrical construction of guides 328, along with the fact that the components of device 324 must fit within a narrower diameter than those of comparable devices for laparoscopic use (such as device 120), device 324 comprises an arrangement of stabilizing wings 330 and support cords 332 that stabilizes the guides upon deployment. This arrangement helps to reduce both radial bending and transverse twisting of the guides, thus ensuring that the needles are ejected through the vessel wall in the proper locations. Wings 330 are fastened together by a collar 334, with a pin 335 that prevents longitudinal movement of the wings along the axis of device 324. The wings typically comprise a superelastic material, such as Nitinol, which is set to assume a curved shape in the austenitic state (as shown in the figures that follow). During insertion and removal of device 324 through tissue 152, however, wings 330 are constrained by tube 336 to remain straight against guides 328, as shown in FIG. 39B, and cords 332 hang loosely between the wings and the guides. Cords 332 typically comprise braided metal wire, such as stainless steel wire, but they may alternatively comprise polymer or silk threads.

FIGS. 40 and 41 are schematic, pictorial illustrations showing suture insertion device 324 in successive stages of the deployment of needle guides 328, in accordance with an embodiment of the present invention. After the distal end of device 324 has been inserted into vessel 320, as shown in FIG. 40, tube 336 is pulled back in the proximal direction, thus releasing wings 330 to curve outward, away from the axis of the tube. Then, as shown in FIG. 41, the guide holder (not shown in this figure) is advanced, pushing guides 328 distally out of the end of tube 336. The superelastic guides likewise assume their curved shapes when released from the tube. Wings 330 extend outward in a direction that is transverse to the plane of guides 328. The guides are typically formed with slightly less curvature than the guides will actually have in their deployed configuration, so as to mechanically preload cords 332 upon deployment. The cords are fastened to guides 328 by couplers 338. The tension of the cords in this configuration prevents radial and transverse movement of the guides.

FIGS. 42-45 are schematic, detail illustrations showing couplers 338 for attaching support cords to needle guide 328, in accordance with embodiments of the present invention. In the embodiment of FIG. 42, coupler 338 comprises a short tubular section 340, with holes cut in its sides to fit over guide 328. Section 340 may be produced by any suitable method known in the art, such as molding or machining by laser or mechanical means. A slot 344 in section 340 captures cord 332 so as to prevent movement of the cord within the coupler. Section 340 is held in place on guide 328 by collars 342, which may be welded, crimped or glued in place or may be formed from superelastic shape memory material, which is heat treated to fit tightly against the guide.

In the embodiment of FIG. 43, coupler 338 comprises a tubular section 350, which fits longitudinally over guide 328. Tubular section 350 has slots 352, which mate with corresponding grooves 354 on guide 328. The slots and grooves are locked together by the pressure of cord 332 between the tubular section and the guide on the opposite side of the guide. Alternatively, cord 332 may be pressed in place against guide 328 by an elastic tubular coupler 360, as shown in FIG. 44. Further alternatively, as shown in FIG. 45, cord 332 may be looped around guide 328 and (if metal cord is used) welded in place. Collars 342 may be used to hold the looped cord in place, and the entire assembly may optionally be coated by a layer of glue 364. Other coupling arrangements will be apparent to those skilled in the art.

Figure 46:
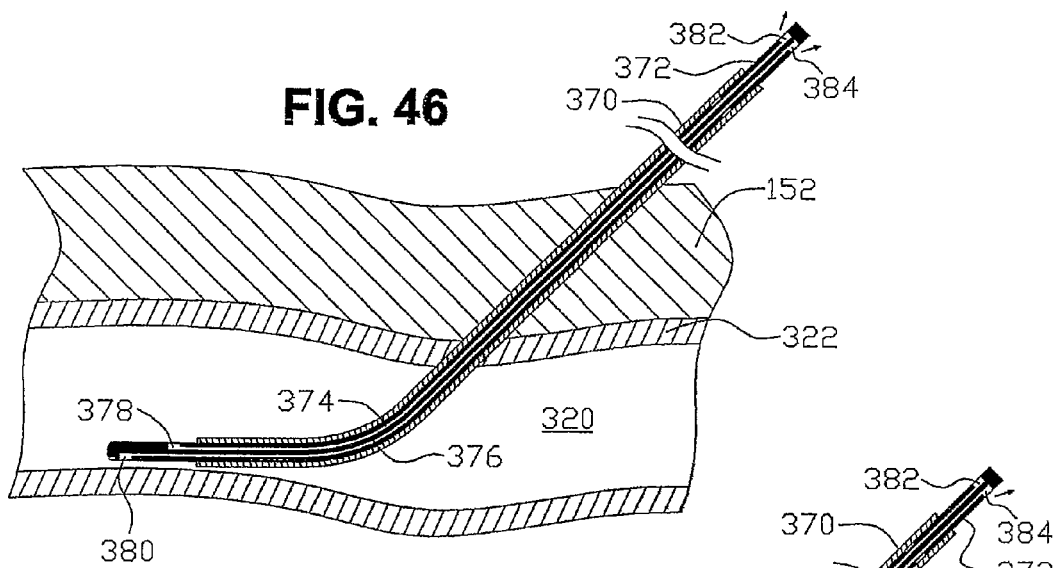
FIGS. 46-48 are schematic, sectional illustrations showing successive stages in the operation of a device for positioning a cannula in a blood vessel prior to suturing, in accordance with an embodiment of the present invention.
Figure 47:
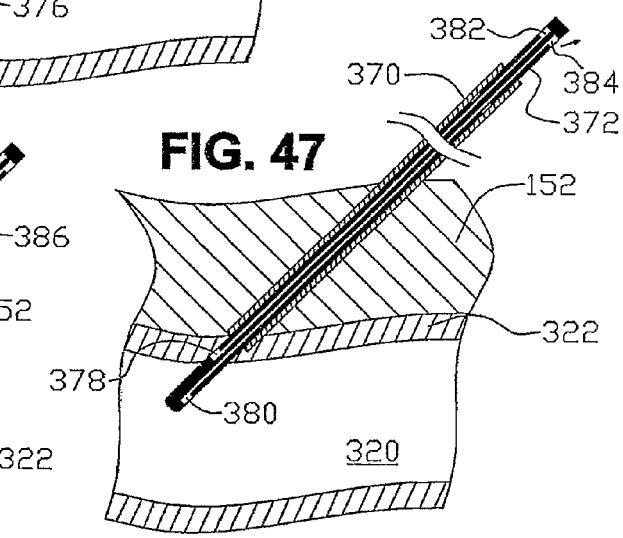
Figure 48:
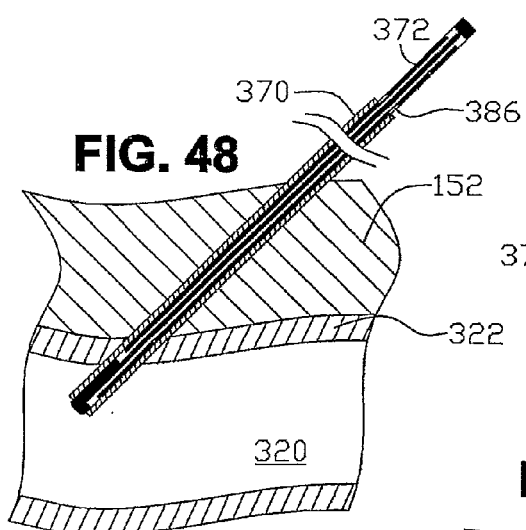

FIGS. 46-48 are schematic, sectional illustrations showing successive stages in the operation of a positioning device 372 for adjusting the position of a cannula 370 in blood vessel 320 prior to suturing, in accordance with an embodiment of the present invention. As noted above, such a cannula is generally used initially for insertion of a catheter into the blood vessel. The sequence of actions shown in FIGS. 46-48 takes place after the catheter has been removed from the patient's body, in preparation for suturing the blood vessel. The purpose of these actions is to position cannula 370 at a proper depth so that when suture insertion device 324 (FIG. 38A) is inserted through the cannula, the distal end of the suture insertion device will be properly located for deployment of needle guides 328.

Positioning device 372 comprises two lumens 374 and 376, having respective distal ports 378, 380 and proximal ports 382, 384. Distal ports 378 and 380 are longitudinally offset, so that port 380 is closer to the distal end of device 372 than port 378. Initially, as shown in FIG. 46, device 372 is inserted through cannula 370 until both of distal ports 378 and 380 protrude through the distal end of the cannula. The practitioner will recognize that device 372 has reached this insertion depth by the outflow of blood through both of proximal ports 382 and 384 (as indicated by the small arrows in FIG. 46).

Now the practitioner withdraws cannula 370, and device 372 along with it, in the proximal direction. When the distal tip of device 372 approaches vessel wall 322, distal port 378 of lumen 374 will be occluded by the vessel wall. Because of the longitudinal offset between the distal ports, however, port 380 still remains in the bloodstream at this point, as shown in FIG. 47. The practitioner will recognize this position by the cessation (or at least reduction) of blood outflow through proximal port 382, while blood continues to flow from port 384. The exact depth of device 372 relative to vessel wall 322 is now known.

Finally, the practitioner advances cannula 370 in the proximal direction, while holding device 372 in place relative to the patient's body, until blood outflow through both of proximal ports 382 and 384 ceases, as shown in FIG. 48. In this position, the distal end of the cannula is precisely aligned with the distal end of device 372, at the proper depth within vessel 320 for subsequent insertion of suture insertion device 324. A mark 386 may also be provided on the shaft of device 372 in order to indicate the proper position of the cannula at this stage. Positioning device 372 is now removed from cannula 370, and suture insertion device 324 is inserted.

Figure 49:
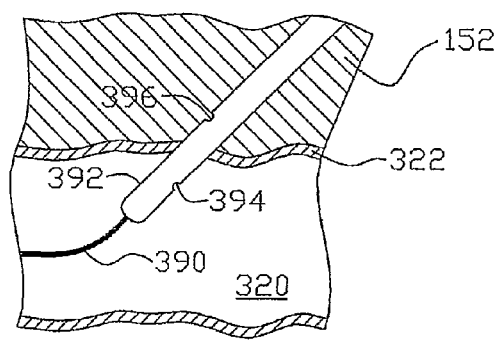
FIG. 49 is a schematic, pictorial illustration showing positioning of a suture insertion device in a blood vessel using a guide wire, in accordance with an embodiment of the present invention.

FIG. 49 is a schematic, pictorial illustration showing positioning of a suture insertion device 392 in blood vessel 320 using a guide wire 390, in accordance with an alternative embodiment of the present invention. Such guide wires are commonly used in catheterization procedures, and device 392 has a lumen (not shown) that permits the device to ride over the guide wire after the catheter has been withdrawn from the body. Although no cannula is shown in this figure, it is also possible to insert the suture insertion device over a guide wire within such a cannula.

Alternatively or additionally, suture insertion device 392 itself may comprise distal ports 394, 396 and lumens (not shown) as in positioning device 372, as an aid to the practitioner in positioning the suture insertion device at the proper depth. In this case, as shown in FIG. 49, the practitioner will know that the suture insertion device is located at the appropriate depth when blood flows out through port 394 but not port 396.

FIG. 50 is a schematic, pictorial illustration showing the distal end of a suture insertion device 400 with four needle guides 402, in accordance with an embodiment of the present invention. Device 400 permits two pairs of needles to be ejected into the target tissue, each pair having a suture connected between them. (The needles and sutures are not shown in the figure for simplicity of illustration.) Thus, device 400 may be used to insert two sutures simultaneously or in immediate succession without removing the device from the body to reload. This arrangement is not only convenient for the practitioner, but also ensures that the sutures will be correctly positioned relative to one another.

FIGS. 51 and 52 are schematic top views of stitch patterns that may be created in vessel wall 322 by suture insertion device 400, in accordance with embodiments of the present invention. Each stitch pattern comprises two sutures 406, which are used to close a puncture 404. In FIG. 51, sutures 406 are side by side. The two sutures may be aligned along the longitudinal axis of the blood vessel and spaced peripherally around the axis. This pattern is achieved by stringing each suture between one of the long guides and one of the short guides to either side of device 400. Alternatively, the sutures may be aligned peripherally and spaced longitudinally along the blood vessel by stringing one of the sutures between the pair of longer guides and the other suture between the pair of shorter guides. Further alternatively, the sutures may be strung crosswise between opposing long/short pairs of guides 402 in order to give crossed stitches in the "X" pattern shown in FIG. 52.

Although FIGS. 50-52 show a certain specific configuration of needle guides 402 and resultant suture patterns, the relative positions and shapes of the needle guides may be modified to provide other suture spacings and patterns as required by other procedures and puncture sizes.

Figure 55:
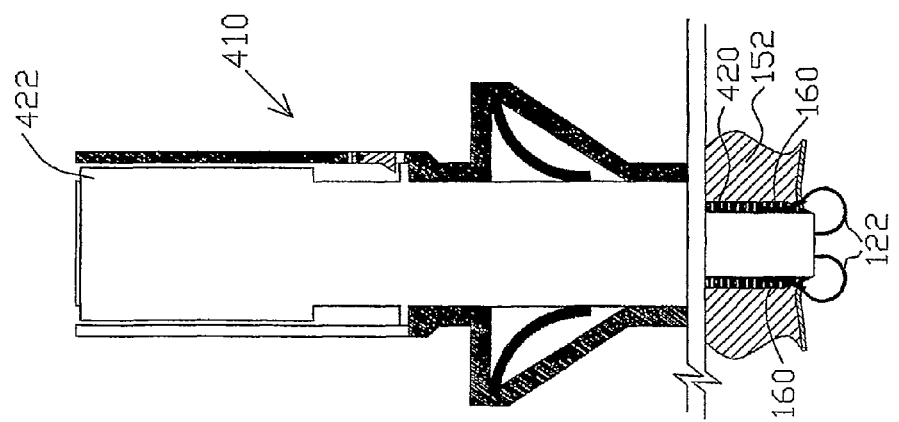
FIGS. 54 and 55 are schematic, sectional illustrations showing stages in the operation of a suture insertion device in conjunction with the trocar of FIG. 53, in accordance with an embodiment of the present invention.
Figure 54:
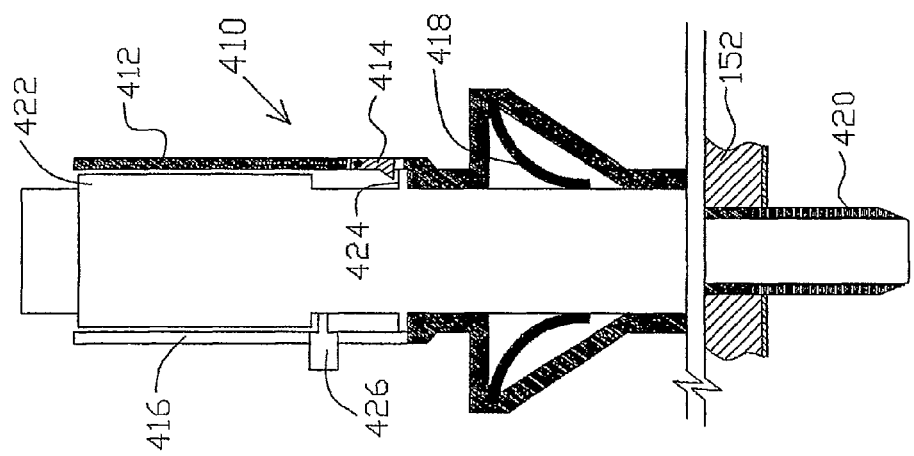
Figure 53:
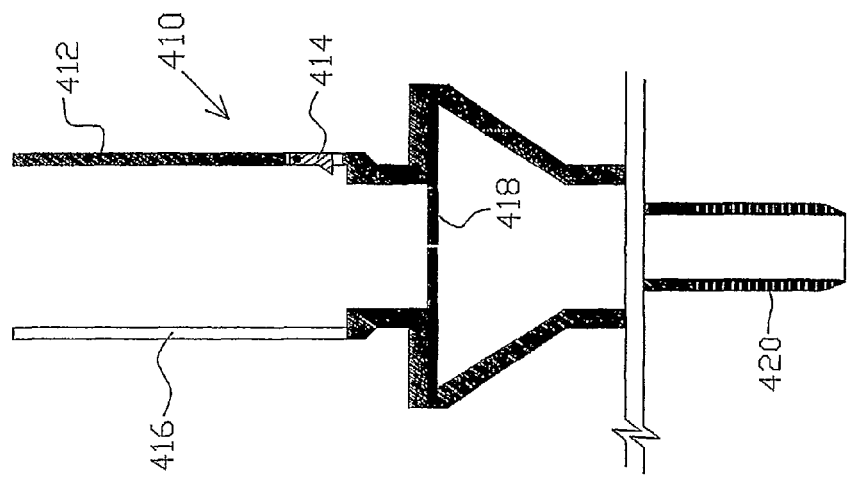
FIG. 53 is a schematic, sectional illustration of a trocar for use with a suture insertion device, in accordance with an embodiment of the present invention.

FIGS. 53-55 are schematic, sectional illustrations of a trocar 410 for use with an integrated suture insertion device 422, in accordance with an embodiment of the present invention. The principles of this embodiment may also be applied to cannulae of other types, such as sheaths used in vascular catheterization. FIG. 53 shows trocar 410 by itself, while FIG. 54 shows the trocar after insertion of device 422. (Device 422, which is shown in outline in order to simplify the illustration, is assumed to be similar in operation to device 120, shown in FIG. 1, aside from the differences that are described hereinbelow.) FIG. 55 shows trocar 410 and device 422 after deployment of needle guides 130 and ejection of needles 160.

Trocar 410 comprises an outer tube 412, which is sized to accept the handle of device 422. A locking clip 414 mates with a ridge 424 on device 422 to hold the device in place inside tube 412. A slot 416 may be provided in outer tube 412 to accommodate controls on the handle of device 422, as well as to ensure proper rotational alignment of the device. The outer tube of the trocar is sealed off from the inner (distal) part by a leaf valve 418, which prevents outflow of gas (from the abdominal cavity during laparoscopy, for example) or fluid (such as blood during vascular catheterization) upon insertion of the trocar into the body. The leaf valve opens inward when the suture insertion device is inserted into the trocar.

The outer surface of the distal end of the trocar may comprise a pliable material 420, such as rubber, which is soft enough to be penetrated by needles 160. Upon ejection of needles 160 from guides 130, as shown in FIG. 55, the needles penetrate and are trapped within material 420. This feature of trocar 410 obviates the need for needle traps 166 (FIG. 10) in the shaft of suture insertion device 422 and thus simplifies the design of device 422. After ejection of the needles, trocar 410 is withdrawn from the patient's body together with device 422, leaving the suture to be tied off by the practitioner. The practitioner may tie and cut the suture manually, as is known in the art, or may alternatively use a dedicated knot pushing device, as described hereinbelow.

Figure 56:
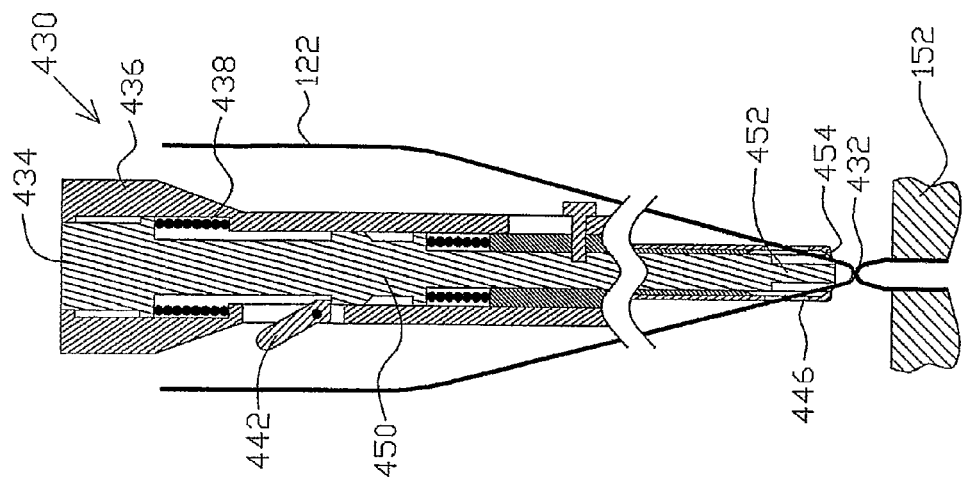
FIG. 56 is a schematic, sectional illustration of a knot pushing and cutting device, in accordance with an embodiment of the present invention.
Figure 57:
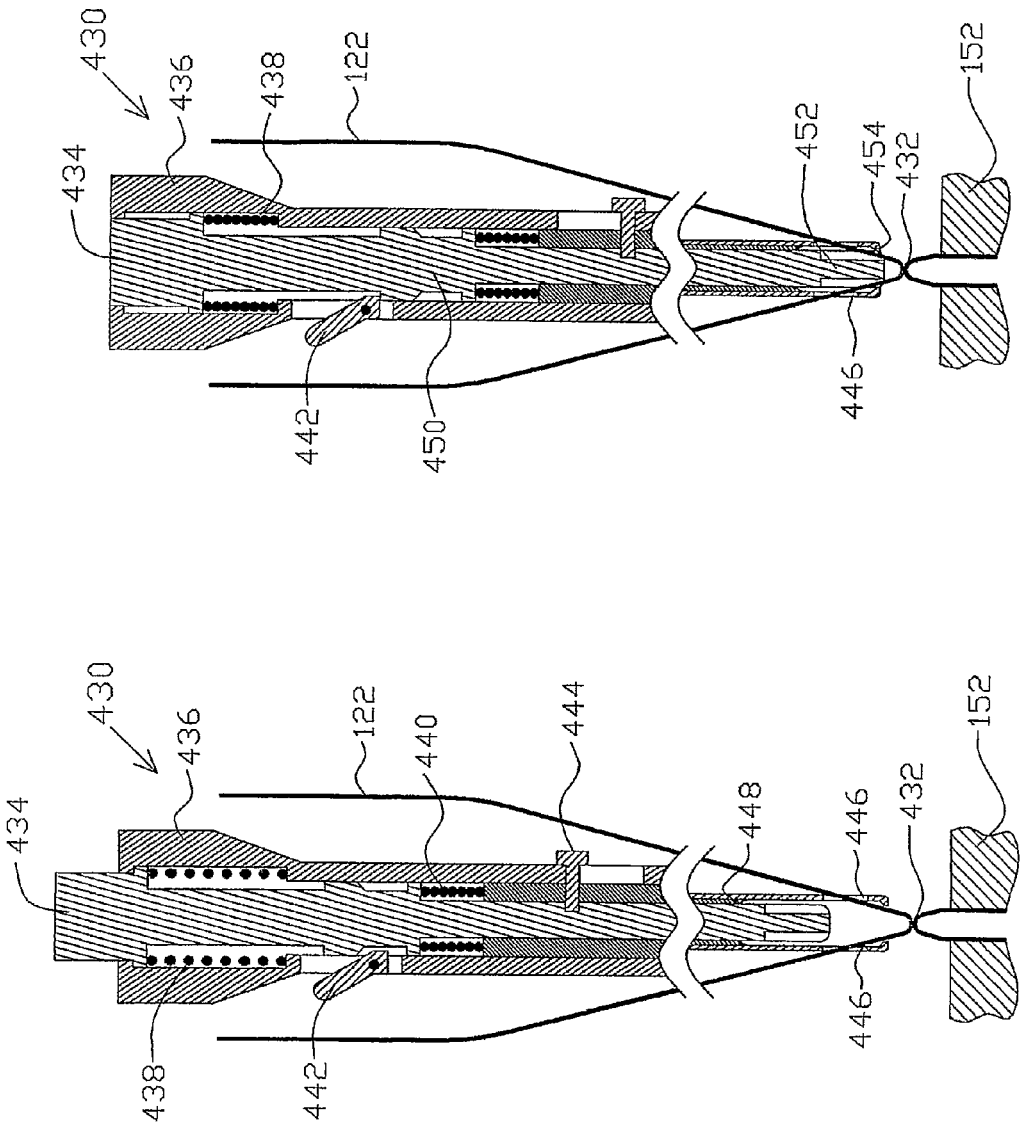

FIGS. 56-59 are schematic, sectional illustrations showing the structure and operation of a knot pushing and cutting device 430, in accordance with an embodiment of the present invention. Device 430 comprises a suture capture mechanism 452 and a suture cutting blade 448. To use device 430, the practitioner makes a sliding knot 432 in suture 122 and then passes the ends of the suture through slits 446 in the sides of the distal end of device 430, as shown in FIG. 56. The practitioner next grasps device 430 by a handle 436 and presses down on a suture capture button 434, as shown in FIG. 57. Pressing this button pushes the rounded lower end of capture mechanism 452 to engage a lower shoulder 454 of device 430. As a result, suture 122 is trapped in slits 446, and knot 432 is prevented from sliding sideways as device 430 presses the knot down through tissue 152. Pressing down on button 434 also compresses a capture spring 438 and locks the capture mechanism in its lowered position by engagement between a ridge 450 on the mechanism and a mating clip 442 on handle 436.

After performing the steps shown in FIGS. 56 and 57, the practitioner pushes device 430 downward through tissue 152 in order to tighten knot 432 against cavity wall 156, as shown in FIG. 58. While pushing the knot downward with one hand, the practitioner holds the ends of suture 122 with the other. In this manner, the suture itself guides the distal end of device 430 down through the tissue to the puncture site. The distal tip of capture mechanism 452 may include a flexible element in order to prevent over-tightening of knot 432.

After tightening down one knot in this manner, the practitioner may choose to make an additional knot in suture 122 before cutting it. To make the additional knot, the practitioner presses clip 442, which releases ridge 450 and thus permits spring 438 to pull mechanism 452 up and away from shoulder 454. The practitioner then withdraws device 430 from tissue 152, ties another knot, and repeats the steps illustrated in FIGS. 56-58 in order to push the second knot down against the first one. These operations may be repeated as many times as desired. Alternatively, if only a single knot is to be made in suture 122, capture spring 438 and clip 442 may be omitted from device 430.

While the practitioner ties and pushes the knots into position, blade 448 is held in place by a pin 444. After tying and tightening the knot (or knots), the physician pulls out pin 444, thus releasing a cutting spring 440. This spring drives blade 448 rapidly downward, so that the blade cuts suture 122 at shoulder 454, as shown in FIG. 59. Optionally, blade 448 may be mounted in a helical groove (not shown) inside the shaft of device 430, so that the blade cuts the suture with a downward rotational motion. Device 430 and the remaining suture are then withdrawn from the body, leaving the suture tied in place, as illustrated in FIG. 14.

FIGS. 60A and 60B are schematic, sectional illustrations showing actuation and re-cocking, respectively, of a knot pushing and cutting device 460, in accordance with another embodiment of the present invention. Device 460 is similar in operation to device 430, as described above, except that device 460 may be used for pushing and cutting multiple sutures. For this purpose, blade 448 in device 460 has a reset handle 464 and a reusable release pin 462. After tightening the knot made in the suture, in the manner described above, the practitioner pulls out pin 462 in order to actuate blade 448, as shown in FIG. 60A. Subsequently, to prepare device 460 for reuse, the practitioner pulls handle 464 upward to re-cock cutting spring 440 and then pushes pin 462 inward in order to lock blade 448 in place. The practitioner presses clip 442 to release capture spring 438, and the device is now ready for reuse.

As another alternative, the features of devices 430 and 460 may be implemented in a two-part knot pusher and cutter, including a single-use shaft and a reusable handle, along the lines of the principles of suture insertion device 290 (FIG. 36A).

Although the embodiments described above relate mainly to suturing of punctures intentionally made by medical practitioners in the course of various minimally-invasive procedures, the principles of the present invention may also be applied in other sorts of surgical procedures and devices. For example, devices similar to those described above may be used in laparoscopic suturing of punctures and other holes in body organs, including both iatrogenic and pathological holes. Applications of this sort may include closure of an iatrogenic rupture of a bile duct, suturing of a perforated ulcer (gastric, duodenal, etc.), suturing of holes left after instrumental colon anastomoses, and sealing of a perforated uterus. Most of these applications at present can be performed only using open surgical techniques. Devices in accordance with embodiments of the present invention may be used to insert any type and number of sutures at once, depending on the diameter and tissue type of the hole.

In other embodiments, devices in accordance with the principles of the present invention may be used in laparoscopic urological procedures, such as uterine suspension for treatment of uterine prolapse. Minimally-invasive sutures can be applied in this manner to secure the uterus in its elevated position. Other possible applications include arthroscopic procedures, such as suturing torn menisci in the knee and rotator cuff tears in the shoulder, as well as minimally-invasive suturing of small lesions in the spine and in the brain, via burr holes in the skull (using suitably miniaturized versions of the devices described hereinabove).

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for suturing tissue adjoining a body cavity in a body of a patient, the method comprising:
providing a shaft having a longitudinal axis and a distal end and having first and second needle guides attached thereto in a first operative configuration in which the needle guides are parallel to the axis, the needle guides holding first and second needles, to which respective first and second ends of a suture thread are attached;
inserting the distal end of the shaft into the body cavity while the needle guides are in the first operative configuration, wherein in the first operative configuration, the needles pointing in a distal direction;
deploying the needle guides outward from the distal end of the shaft into the body cavity so that the needle guides assume a second operative configuration in which the needles held by the needle guides point in a proximal direction, wherein the needle guides curved out of the shaft so as to point in the proximal direction toward the shaft;

ejecting the needles from the needle guides in the second operative configuration so as to cause the needles to penetrate the tissue adjoining the body cavity; and capturing and holding the first and second ends of the suture thread with the shaft after the needles have passed through the tissue.

2. The method according to claim 1, wherein the needles have respective points, and wherein the needle guides contain the needles so that the points do not contact the tissue while the needles are held by the needle guides.

3. The method according to claim 2, wherein the needle guides have respective outer ends, and comprising bringing the outer ends of the needle guides in the second operative configuration into engagement with the tissue before ejecting the needles.

4. The method according to claim 3, wherein bringing the outer ends of the needle guides into engagement with the tissue comprises pulling the shaft in the proximal direction so as to create tension in the tissue by pressure of the outer ends of the needle guides against the tissue before ejecting the needles.

5. The method according to claim 1, and comprising, after ejecting the needles through the tissue, pulling the shaft together with the needles and the needle guides in the proximal direction so as to remove the shaft, the needles, the needle guides and the ends of the suture thread from the body while the suture thread tightens through the tissue.

6. The method according to claim 5, wherein inserting the distal end of the shaft comprises introducing the distal end of the shaft through a puncture in the tissue, and comprising tying the suture thread after pulling the shaft together with the needles and the needle guides in the proximal direction so as to close the puncture.

7. The method according to claim 6, wherein introducing the distal end comprises inserting the distal end of the shaft through a laparoscopic puncture port, and wherein tying the suture thread comprises closing the laparoscopic puncture port.

8. The method according to claim 6, wherein introducing the distal end comprises inserting the distal end of the shaft into a blood vessel, and wherein tying the suture thread comprises closing the puncture in a blood vessel wall.

9. The method according to claim 8, wherein inserting the distal end of the shaft into the blood vessel comprises passing the distal end of the shaft through the puncture at an oblique angle relative to the blood vessel wall, and wherein ejecting the needles comprises passing the first and second needles through the blood vessel wall at respective first and second locations that are longitudinally spaced along a length of the blood vessel, so that the suture thread, when tied, is parallel to a longitudinal axis of the blood vessel.

10. The method according to claim 1, wherein deploying the needle guides comprises pushing the needle guides out through the distal end of the shaft, whereupon the needle guides curve back in the proximal direction.

11. The method according to claim 1, wherein the needle guides comprise a superelastic material, which is formed so as to have a curved shape when deployed from the shaft.

12. The method according to claim 1 wherein the needles comprise an elastic material, which is formed so that the needles assume a straight shape upon being ejected from the needle guides.

13. The method according to claim 1, wherein deploying the needle guides comprises deploying one or more stabilizers, which are contained within the shaft while the needle guides are in the first operative configuration, so as to stabilize the needle guides in the second operative configuration.

14. The method according to claim 1, wherein the first and second needle guides are non-symmetrical in the second operative configuration.

15. The method according to claim 14, wherein the needle guides have respective outer ends, and comprising, after deploying the needle guides, bringing the outer ends of the first and second needle guides into simultaneous engagement with the tissue while the shaft is angled obliquely relative to the tissue, wherein ejecting the needles comprises ejecting the needles while the first and second needle guides are in the simultaneous engagement with the tissue and the shaft is angled obliquely.

16. The method according to claim 1, wherein the suture thread held by the first and second needles is a first thread, and wherein providing the shaft comprises providing third and fourth needle guides attached to the shaft and providing third and fourth needles, which are respectively held by the third and fourth needle guides and hold a second suture thread, and wherein the ejecting the needles comprises ejecting the first, second, third and fourth needles, thereby passing the ends of both the first and second suture threads through the tissue.

17. The method according to claim 16, wherein ejecting the first, second, third and fourth needles comprises making two parallel stitches through the tissue.

18. The method according to claim 16, wherein ejecting the first, second, third and fourth needles comprises making two crossed stitches through the tissue.

19. The method according to claim 1, wherein the needles are formed from a plate of a flat material.

20. The method according to claim 1, wherein each of the needles comprises a tube.

21. The method according to claim 1, wherein ejecting the needles comprises aiming the needles toward the shaft, and comprising capturing and holding the needles against the shaft after the needles have penetrated the tissue.

22. The method according to claim 21, wherein deploying the needle guides comprises configuring the needle guides to point the needles toward the shaft, so that the needles strike the shaft after passing through the tissue.

23. The method according to claim 1, wherein ejecting the needles comprises actuating an ejector so as to drive first and second ejector ends into the first and second needle guides, respectively, in order to eject the needles.

24. The method according to claim 23, wherein actuating the ejector comprises coupling the ejector to the needle guides so that the ejector cannot be actuated when the needle guides are in the second operative configuration.

25. The method according to claim 1, and comprising returning the needle guides to the first operative configuration after ejection of the needles, and withdrawing the shaft from the body while the needle guides are in the first operative configuration.

26. The method according to claim 25, wherein ejecting the needles comprises actuating an ejector, and wherein returning the needle guides comprises coupling the ejector to the needle guides so that actuation of the ejector causes the needle guides to return to the first operative configuration automatically.

27. The method according to claim 1, wherein providing the shaft comprises coupling a handle to the shaft, the handle comprising controls for use by an operator, and comprising, after ejecting the needles and removing the shaft from the body, releasing the shaft from the handle and replacing the shaft.

28. The method according to claim 1, wherein providing the shaft comprises holding the needle guides inside the shaft in the first operative configuration.

29. The method according to claim 28, wherein ejecting the needles comprises withdrawing the needle guides automatically into the shaft after ejection of the needles.

30. The method according to claim 1, wherein inserting the distal end comprises passing a cannula from a body surface through a puncture into the body cavity, and inserting the shaft through a lumen of the cannula.

31. The method according to claim 1, wherein the shaft contains a lumen, and wherein inserting the distal end comprises passing the shaft into the body cavity over the guide wire.

32. The method according to claim 1, wherein the shaft contains first and second lumens having respective first and second ports disposed along the shaft at different, respective longitudinal positions, and wherein inserting the shaft comprises observing a flow of a body fluid from the cavity through the first and second lumens in order to adjust a depth of insertion of the shaft inside the body cavity.

* * * * *